US006140052A

United States Patent [19]
He et al.

[11] Patent Number: 6,140,052
[45] Date of Patent: Oct. 31, 2000

[54] CMYC IS REGULATED BY TCF-4

[75] Inventors: Tong-Chuan He, Chicago, Ill.; Bert Vogelstein, Baltimore; Kenneth W. Kinzler, BelAir, both of Md.

[73] Assignee: The Johns Hopkins University, Baltimore, Md.

[21] Appl. No.: 09/136,605

[22] Filed: Aug. 20, 1998

Related U.S. Application Data

[63] Continuation-in-part of application No. 08/821,355, Mar. 20, 1997, Pat. No. 5,851,775.
[51] Int. Cl.[7] .............................. C12Q 1/68; C12N 5/10
[52] U.S. Cl. ............................... 435/6; 435/325; 435/366
[58] Field of Search ................................. 435/6, 325, 366

[56] References Cited

U.S. PATENT DOCUMENTS 5,851,775   12/1998   Barker et al. ............................... 435/6

FOREIGN PATENT DOCUMENTS 98 41631   9/1998   WIPO .

OTHER PUBLICATIONS

Curt Suplee, The Washington Post, Key Process In Cancer Is Identified, Finding May Facilitate Early Detection, Therapy, 2–4 (1997).
Bonnee Rubinfeld et al. The Journal of Biological Chemistry, "The APC Protein and E–cadherin Form Similar but Independent Complexes with α–Catenin, β–Catenin, and Plakoglobin", vol. 270, No. 10, pp. 5549–5555 (1995).
J. Kawanishi et al., Molecular and Cellular Biology, "Loss of E–Cadherin–Dependent Cell–Cell Adhesion due to Mutation of the β–Catenin Gene in a Human Cancer Cell Line, HSC–39" vol. 15, No. 3, pp. 1175–1181 (1995).
P.F. Robins, J. Exp. Med., "A Mutated β–Catenin Gene Encodes a Melanoma–specific Antigen Recognized by Tumor Infiltrating Lymphocytes", vol. 183, pp. 1185–1192 (1996).
B. Rubinfeld et al., Science, "Association of the APC Gene Product with β–Catenin", vol. 262, pp. 1731–1734 (1993).
L.K. Su et al., Science, "Association of the APC Tumor Suppressor Protein with Catenins", vol. 262, pp. 1734–1737 (1993).
Bonnee Rubinfeld et al., Science, "Binding of GSK3β to the APC–β–Catenin Complex and Regulation of Complex Assembly", vol. 272, pp. 1023–1026 (1996).
Susan Munemitsu et al., Proc. Natl. Acad. Sci., "Regulation of intracellular β–catenin levels by the adenomatous *polyposis coli* (APC) tumor–suppressor protein", vol. 92, pp. 3046–3050 (1995).
Jurgen Behrens et al., "Functional interaction of β–catenin with the transcription factor LEF–1" vol. 382, pp. 638–642 (1996).
Otmar Huber et al., Mech. Dev., "Nuclear localization of β–catenin by interaction with transcription factor LEF–1", vol. 59, pp. 3–10 (1996).
Miranda Molenaar, Cell, "XTcf–3 Transcription Factor Mediates βCatenin–Induced Axis Formation in Xenopus Embryos", vol. 86, (1996).
J. Castrop et al. "A Gene Family of HMG–box transcription factors with homology to tcf–1" Nucleic Acid Research, vol. 20, No. 3, 1992, p. 611.
L. Hillier et al. "The WashU–Merck EST Project" EMBL Sequence Data Library, Sep. 6, 1996.
J. Catrop et al. "A Gene Family of HMG–box transcription factors with homology to tcf–1", EMBL Sequence Data Library, Nov. 22, 1993.
K.W. Kinzler and B. Vogelstein, "Lessons from hereditary colorectal cancer", Cell, vol 87, Oct. 18, 1996, pp. 159–170.
M. Molenaar et al. "XTcf–3 transcription factor mediates beta–catenin–induced axis formation in xenopus embryos" Cell, vol. 86, Aug. 1996, pp. 391–399.
M. Van De Wetering et al. "Identification and Cloning of TCF–1, a t lymphocyte–specific transcription factor containing a sequence–specific hmg–bo" The EMBO Journal, vol. 10, No. 1, 1991, pp. 123–132.
J. Behrens et al. "Functional interaction of bta–catenin with the transcription factor LEF–1" Nature, vol. 382, 1996, pp. 638–642.
V. Korinek et al. "Constitutive transcriptional activation by a beta–catenin–Tcf complex in APC–/–colon carcinoma" Science, vol. 275, Mar. 21, 1997, pp. 1784–1787.
H. Clevers and M. Van De Wetering, "TCF/LEF factors earn their wings" Trends in Genetics, vol. 13, No. 12, Dec. 1997, pp. 485–489.
Korinek et al. (1997) GenBank, Accession No. Y11306, Aug. 14, 1997 accessed Aug. 24, 1998.
Morin et al. "Activation of beta–catenin–tcf signaling in colon cancer by mutations in beta–catenin of APC" Science, US American Association for the Advancement of Science, vol. 275, Mar. 1997 pp. 1787–1790.

(List continued on next page.)

*Primary Examiner*—Robert A. Schwartzman
*Attorney, Agent, or Firm*—Banner & Witcoff, Ltd.

[57]   ABSTRACT

The APC tumor suppressor protein binds to β-catenin, a protein recently shown to interact with Tcf/Lef transcription factors. Here, the gene encoding a Tcf family member that is expressed in colonic epithelium (hTcf-4) was cloned and characterized. hTcf-4 transactivates transcription only when associated with β-catenin. Nuclei of APC$^{-/-}$ colon carcinoma cells were found to contain a stable β-catenin-hTCF-4 complex that was constitutively active, as measured by transcription of a Tcf reporter gene. Reintroduction of APC removed β-catenin from hTcf4 and abrogated the transcriptional transactivation. Constitutive transcription of TCF target genes, caused by loss of APC function, may be a crucial event in the early transformation of colonic epithelium. It is also shown here that the products of mutant APC genes found in colorectal tumors are defective in regulating β-catenin/Tcf-4 transcriptional activation. Furthermore, colorectal tumors with intact APC genes were shown to contain subtle activating mutations of β-catenin that altered functionally significant phosphorylation sites. These results indicate that regulation of β-catenin is critical to APC's tumor suppressive effect and that this regulation can be circumvented by mutations in either APC or β-catenin.

26 Claims, 19 Drawing Sheets

OTHER PUBLICATIONS

Zou et al. "Positive and Negative Regulation of c–MYC Transcription" Curr top Microbiol Immunol. vol. 224, 1997, pp. 57–66.

Marcu et al. "Differential Regulation of the C–MYC P1 and P2 Promoters in the Absence of Functional Tumor Suppressors. Implications for the Mechansim of Dergulated MYC Transcription" Curr. Top Microbiol Immunol. vol. 224, 1997, pp. 47–56.

Geltinger et al. "Tata Box and SP1 Sites Mediate the Activation of c–MYC Promoter P1 by Immunoglobulin Kappa Enhancers" Gene Expression, vol. 6, 1996, pp. 113–127.

Sparks et al. "Mutational analysis of the APC/beta–catenin/Tcf pathway in colorectal cancer" Cancer Research, US American association for Cancer Research, vol. 58, Mar. 1998 pp. 1130–1134.

He et al. "Identification of c–MYC as a Target of the APC Pathway" Science, vol. 281, Sep. 1998, pp. 1509–1512.

Rosemary Watt et al. "The structure and nucleotide sequence of the 5' end of the human c–myc oncogene" Proc. Natl. Acad. Sci. USA, vol. 80, pp. 6307–6311 Oct. 1983

Calude Gazin et al. "Nucleotide sequence of the human c–myc locus: provacative open reading frame within the first exon" EMBO Journal, vol. 3 (3) pp. 383–7 1984.

Lawrence W. Stanton et al. "Nucleotide sequence of the human N–myc gene" Proc. Natl. Acad. Sci., USA vol. 83, pp. 1772–1776, Mar. 1986.

FIG. 1A

```
hTCF-4E
hTCF-1E

```
194  PPHLPADVDPKTGIPRPPHPPDISPYYPLSPGTV:GQIPHP
173  TP  APADISQK QVHRPLQTPDLSGFYS:MGQLPHT
234  LGWLVPQQGQPVYPITTGFRH PYPTALTVNASVSRF
211  VSWPSP PLYPLSP SCGYRQHFPAPTA APGAPYPRFTH
271  PPHMVPPHHTLHTTGIPHPAIVTPTV:SDVGSLHS
248  PSLMLGSGVPGHPAAIPHPAA SSQSDVGSLHS
                        :  :  :  GKQ  LQPFDRNL
311  SKHQ DSKKEEKKPH IKKPLNAFMLYMKEMRAKVVAEC
285  KTQ AESKAEKEAKK  KKPLNAFMLYMKEMRAKVIAEC
350  TLKES AAINQ ILGRRWHALSREEQAKYYELARKERQLHMQ
324  TLKES AAINQ ILGRRWHALSREEQAKYYELARKERQLHMQ
390  LYPGWSARDNYGKKKKRRKRDKQPGETNEHSECFLNPCLSL
364  LYPGWSARDNYGKKKKRRS:REK       HQE          S
430  PPITDLSAPKKCRARFGLDQQNNWCGPCRRKKCVRYIQG
389  TTDPGSPKKCRARFGLNQQTDWCGPCRRKKCIRYLPG
```

FIG. 1C

```
470 EGSCLSPPSSDGSLLDSPPPSPNLLGSPPPRDAKSQTEQTQ
427 EGRCPSPVPSDDSAL GCPGSPAPQDS PSYHLLPRFPPTE
510 PLSLSLKPDP LAHLS MMPPPPALLLAEATHKASALCP
465 LLTSPAEPAPTSPGLSTALSLPTPGPPPQAPRSTLQSTQVQ
547 NGALDLPPAALQPAAPSSSIAQPSTSWLHSHSSLAGTQPQ
505 QQESQRQVA*
587 PLSLVTKSLE* hTCF-4B
hTCF-1B
390 LYPGWSARDNYGKKKKRKRDKQPGETNGEKKSAFATYKVK
364 LYPGWSARDNYGKKKRRSREKHQESTTGGKRNAFGTYPEK

430 AAASAHPLQMEAY*
404 AAAPAPFFLPMTVL*
```

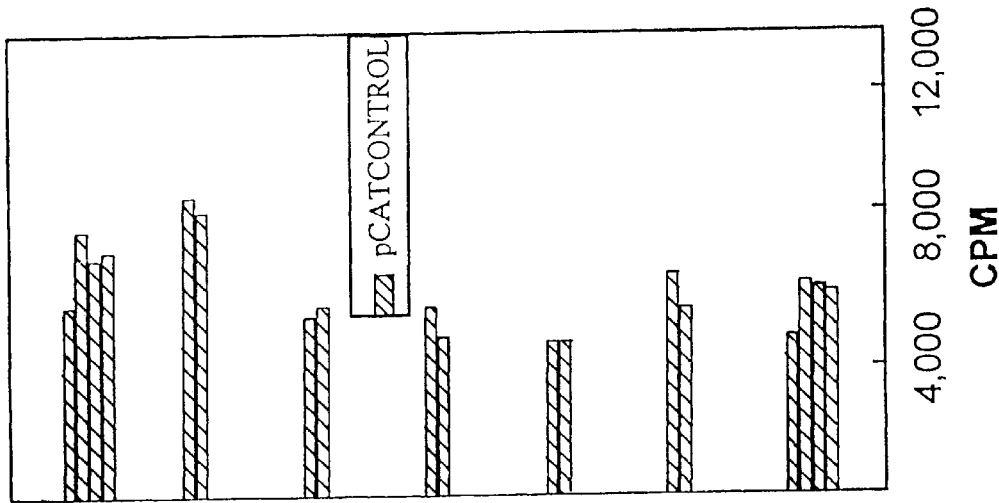
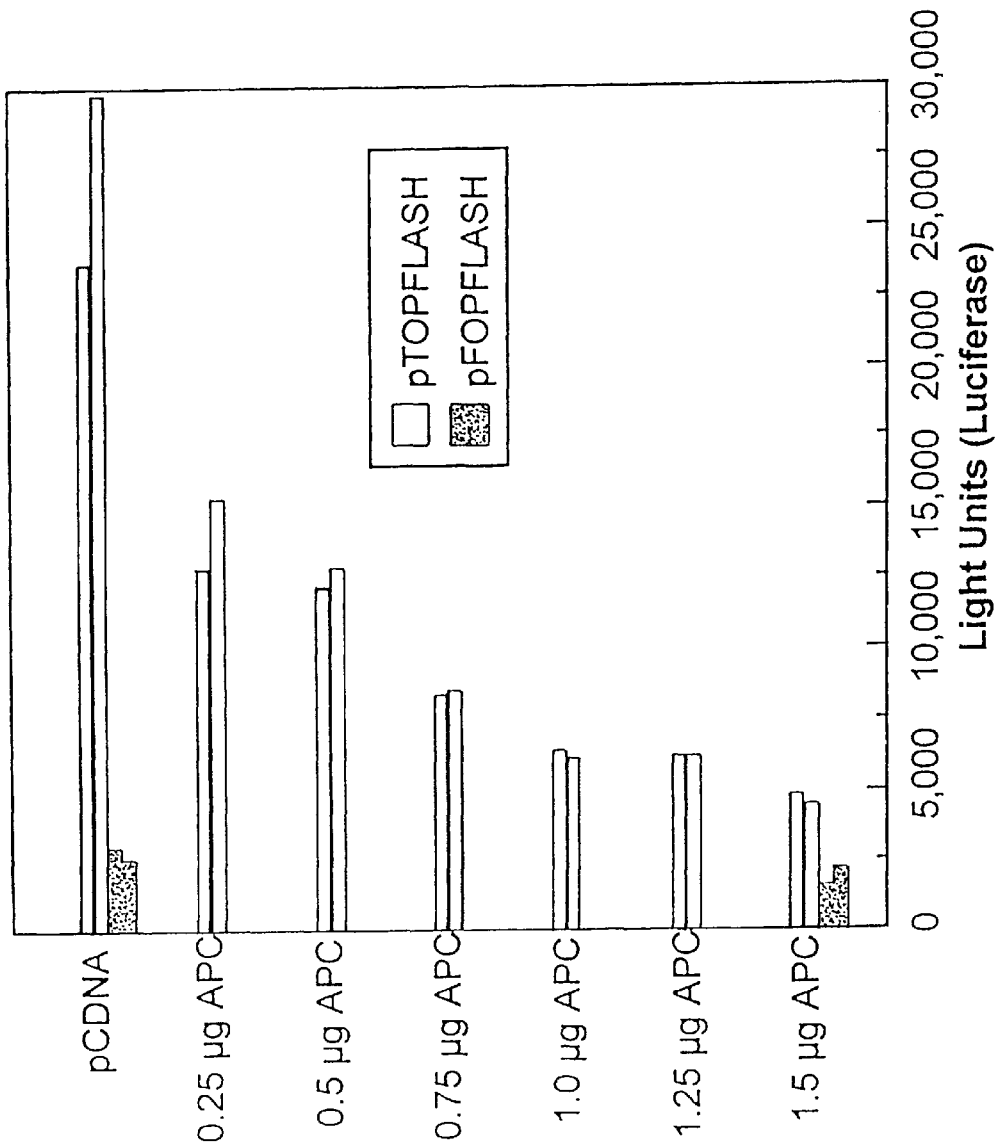

TBE1  CCTTTGATC  GCTTTGATC TBE2
TBE1m CCTTTG<u>G</u><u>C</u>C  GCTTTG<u>G</u><u>C</u>C TBE2m ns
CM YC IS REGULATED BY TCF-4

This application is a continuation-in-part of application Ser. No. 08/821,355, filed Mar. 20, 1997, now U.S. Pat. No. 5,851,775.

The U.S. Government has a paid-up license in this invention and the right in limited circumstances to require the patent owner to license others on reasonable terms as provided for by the terms of grant CA57345 awarded by the National Institutes of Health.

TECHNICAL FIELD OF THE INVENTION

This invention is related to the field of cancer diagnostics and therapeutics. More particularly it relates to methods for diagnosing and treating cancers associated with APC or β-catenin mutations.

BACKGROUND OF THE INVENTION

Mutations of the adenomatous polyposis coli (APC) gene are the most common disease-causing genetic events in humans; approximately 50% of the population will develop colorectal polyps initiated by such mutations during a normal life span (14). Individuals who inherit APC mutations develop thousands of colorectal tumors, consistent with APC's tumor suppressor or "gatekeeping" role in colorectal tumorigenesis (15,16). APC homodimerizes through its amino-terminus (17), and interacts with at least six other proteins: β-catenin (18), γ-catenin (plakoglobin) (19), tubulin (20), EB1 (21), hDLG, a homologue of a Drosophila tumor suppressor protein (22), and ZW3/GSK3β kinase (23). Whether any of these interacting proteins communicate APC growth-controlling signals is unknown. Thus there is a need in the art for a fuller understanding of how the tumor suppressor gene APC functions in cells.

SUMMARY OF THE INVENTION

It is an object of the present invention to provide human nucleotide sequences encoding transcriptional activation proteins.

It is another object of the present invention to provide isolated preparations of transcriptional activation proteins.

It is an object of the present invention to provide methods of determining the presence or absence in a cell of wild-type APC or a downstream protein in the APC transcription regulatory pathway.

Another object of the invention is to provide methods of identifying candidate drugs for use in Familial Adenomatous Polyposis (FAP) patients or patients with increased risk of developing cancer.

It is yet another object of the invention to provide methods of identifying candidate drugs for the treatment of cancer patients, in particular those with APC or β-catenin mutations.

Another object of the invention is to provide a method for diagnosing cancer in a sample suspected of being neoplastic.

Another object of the invention is to provide a method for treating a patient with colorectal cancer or other cancer associated with FAP.

These and other objects of the invention are achieved by providing one or more of the embodiments described below. In one embodiment of the invention an intron-free DNA molecule is provided which encodes Tcf-4 protein as shown in SEQ ID NO: 5 or 6.

According to another embodiment of the invention an isolated Tcf-4 protein is provided. The protein is substantially free of other human proteins, and has a sequence as shown in SEQ ID NO: 2 or 4.

In another embodiment of the invention a method is provided for determining the presence or absence in a cell of wild-type APC or a downstream protein in the APC transcription regulatory pathway. The method comprises the steps of:

introducing a Tcf-responsive reporter gene into the cell; and measuring transcription of said reporter gene; wherein a cell which supports active transcription of said reporter gene does not have wild-type APC or does not have a wild-type downstream protein in the APC transcription regulatory pathway.

According to yet another embodiment of the invention a method is provided for determining the presence or absence in a cell of wild-type APC. The method comprises the steps of:

contacting a Tcf-responsive reporter gene with a lysate of the cell; and measuring transcription of said reporter gene; wherein a lysate which inhibits said transcription has wild-type APC.

In still another embodiment of the invention a method of identifying candidate drugs is provided. The drugs may be useful for treatment of FAP or other cancer patients or patients with increased risk of developing cancer. The method comprises the steps of:

contacting a cell having no wild-type APC or a mutant β-catenin with a test compound;

measuring transcription of a Tcf-responsive reporter gene, wherein a test compound which inhibits the transcription of the reporter gene is a candidate drug for cancer therapy.

According to yet another aspect of the invention another method is provided for identifying candidate drugs for use in for use in FAP patients, colon cancer patients, patients with mutations in β-catenin or APC, or patients with increased risk of developing cancer. The method, comprises the steps of:

contacting a Tcf-responsive reporter gene with a test compound under conditions in which the reporter gene is transcribed in the absence of the test compound; and measuring transcription of the Tcf-responsive reporter gene; wherein a test compound which inhibits said transcription is a candidate drug for cancer therapy.

According to another aspect of the invention a method is provided for identifying candidate drugs for use in FAP patients or patients with increased risk of developing cancer. The method comprises the steps of:

contacting a test compound with β-catenin and Tcf-4 under conditions in which β-catenin and Tcf-4 bind to each other; and determining whether the test compound inhibits the binding of β-catenin and Tcf-4, a test compound which inhibits the binding being a candidate for cancer therapy or prophylaxis.

According to still another embodiment of the invention a method is provided for diagnosing cancer in a sample suspected of being neoplastic. The method comprises the steps of:

comparing a CTNNB sequence found in the sample to a second CTNNB sequence found in a normal tissue, wherein a difference between the first and second sequence is an indicator of cancer.

According to another aspect of the invention a method is provided for treating a patient with colorectal cancer or other cancer associated with FAP. The method comprises the step of:

administering to the patient a nucleotide sequence comprising a portion of the APC coding sequence, said portion consisting of the β-catenin binding site.

According to another aspect of the invention a method is provided for treating a patient with colorectal cancer or other cancer associated with FAP. The method comprises the step of:

administering to the patient a polypeptide comprising a portion of the APC coding sequence, said portion consisting of the β-catenin binding site.

The present invention thus provides the art with diagnostic, therapeutic and drug discovery methods especially useful for FAP and other cancers with APC or β-catenin mutations.

BRIEF DESCRIPTION OF THE DRAWINGS

FIGS. 1A, 1B, and 1C. Sequence comparison of hTcf-4 (SEQ ID NOS 5, 6; odd numbered lines) and hTcf-1 (SEQ ID NO: 8, 9; even numbered lines).

Two alternative splice forms of hTcf-4 were identified, each encoding a different COOH-terminus. One form (hTcf-4E) was homologous to hTCF-1E (top) (7); the other form (hTcf-4B) was homologous to hTcf-1B (bottom; FIG. 1C). The highly conserved $NH_2$-terminal interaction domain and the High-Mobility Group (HMG) box DNA-binding region are boxed. Abbreviations for the amino acids are: A Ala; C, Cys; D, Asp; E, Glu; F, Phe; G, Gly; H, His; I, Ile; IC, Lys; L, Leu; M, Met; N, Asn; P, Pro; Q, Gln; P, Arg; S, Ser; T, Thr; V, Val; W, Trp; and Y, Tyr. The nucleotide sequence has been deposited in GenBank (accession number:AR067645-42)

(FIG. 2A) Northern blot analysis of hTcf-4, hTcf-1, hLef-I expression in Jurkat T cells (lane 1); colonic mucosa (lane 2); colon carcinoma cell lines DLD-1 (lane 3), HCT116 lane 4); SW480 (lane 5); SW620 (lane 6); HT29 (lane 7). Lane 2 contains 5 μg total RNA; all others contain 15 μg total RNA. The positions of 18S and 28S ribosomal RNAs are shown. EtBr, ethidium bromide stain. (FIG. 2B) In situ hybridization of healthy human colon tissue to an hTcf-4 probe. (FIG. 2C) In situ hybridization to a negative control probe (a fragment of the E. coli neomycin resistance gene).

FIGS. 3A, 3B, and 3C. Transactivational properties of β-catenin/hTcf-4.

All reporter assays were performed as duplicate transfections. For each condition, both values are shown. (FIG. 3A) Reporter gene assays in IIA1.6 B cells. Cells were by electroporation with 1 μg luciferase reporter plasmid, 5 μg β-catenin expression plasmid, and 3II-hTcf-4 expression plasmids. Empty pCDNA was added to a total of 10 μg, plasmid DNA. (FIG. 3B) Reporter gene assays in SW480 colon carcinoma cells. Cells were transfected with 0.3 μg, of the indicated luciferase reporter gene, 0.7 μg pCATCONTROL as internal control, the indicated amounts of pCMVNeo-APC, and empty PCDNA to a total of 2.5 μg plasmid DNA Control CAT values are given in the right panel.

(FIG. 5A) Schematics of wild-type (WT) and mutant APC. APC is a 2843-amino-acid (AA) protein (32) with contains armadillo (ARM) repeats in the amino-terminus (33), 15 and 20 AA β-catenin-binding repeats in the central region (18, 19), and a basic region in the carboxyl-terminus (32). The carboxyl-terminus also contains a TXV sequence which mediates DLG binding (22). (FIG. 5B) Effects of WT and mutant APC on CRT. SW480 cells containing endogenous mutant APC were transfected with the APC expression vectors shown in (FIG. 5A) and CRT was measured. Cells were transfected with increasing amounts of WT APC (0, 0.15 and 0.5 μg) or 0.5 μg mutant APC. CRT reporter activities are expressed relative to assays containing no WT APC and are the means of three replicates. Error bars represent standard deviations.

Lipofectamine was used to cotransfect SW480 cells with an internal control (0.5 μg pCMV-βgal), a reporter construct (0.5 μg pTOPFLASH or pFOPFLASH) and the indicated amount of the various APC expression vectors. The pTOPFLASH reporter contained an optimized Tcf-binding site 5' of a luciferase reporter gene, whereas pFOPFLASH contained a mutated site that does not bind Tcf. The amount of DNA in each transfection was kept constant by addition of an appropriate amount of empty expression vector (pCEP4). Luciferase and β-galactosidase activities were determined 16 hours after transfection. Luciferase activity was corrected for transfection efficiency (using the control β-galactosidase activity) and nonspecific transcription (using the pFOPFLASH control).

Figure 5A:
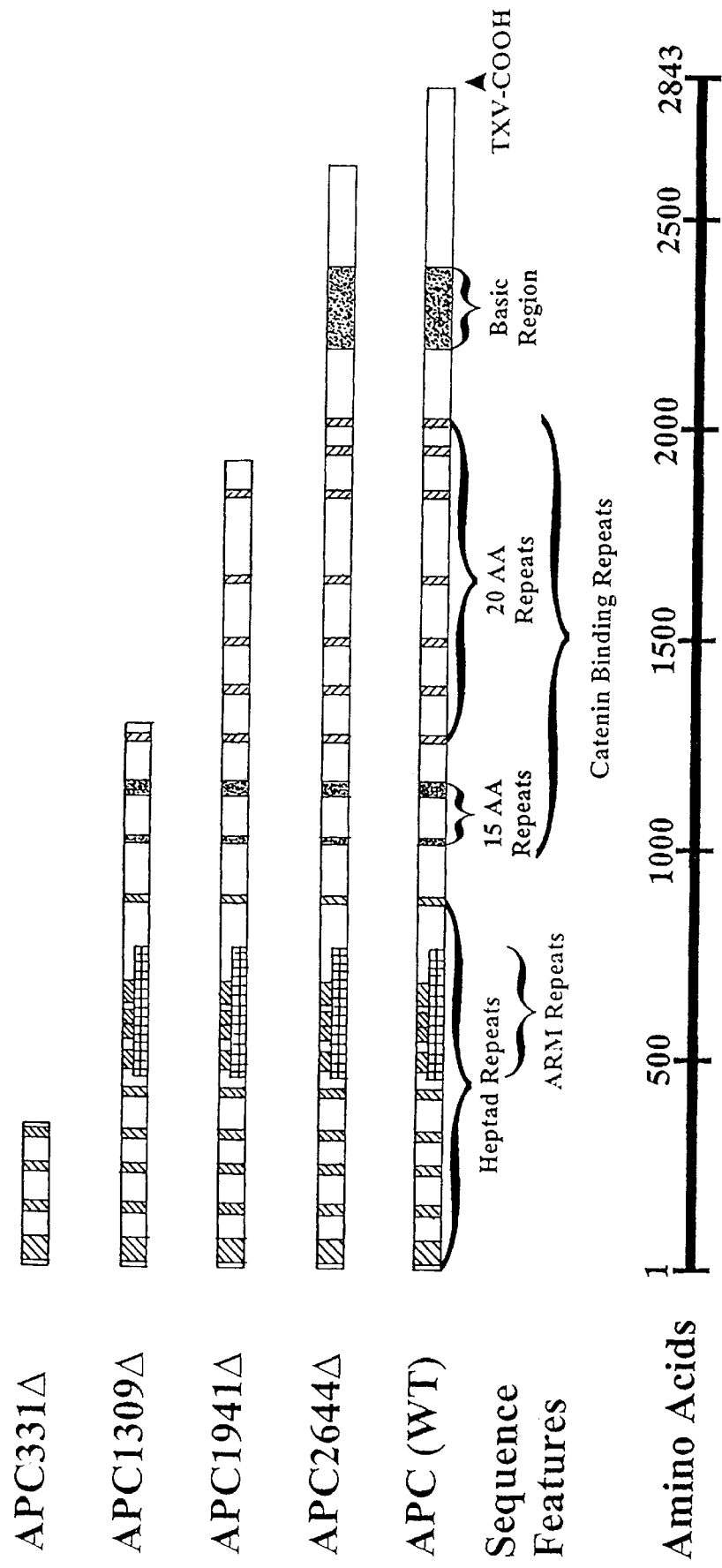
FIGS. 5A and 5B. Effects of APC mutations on CRT.
Figure 5B:
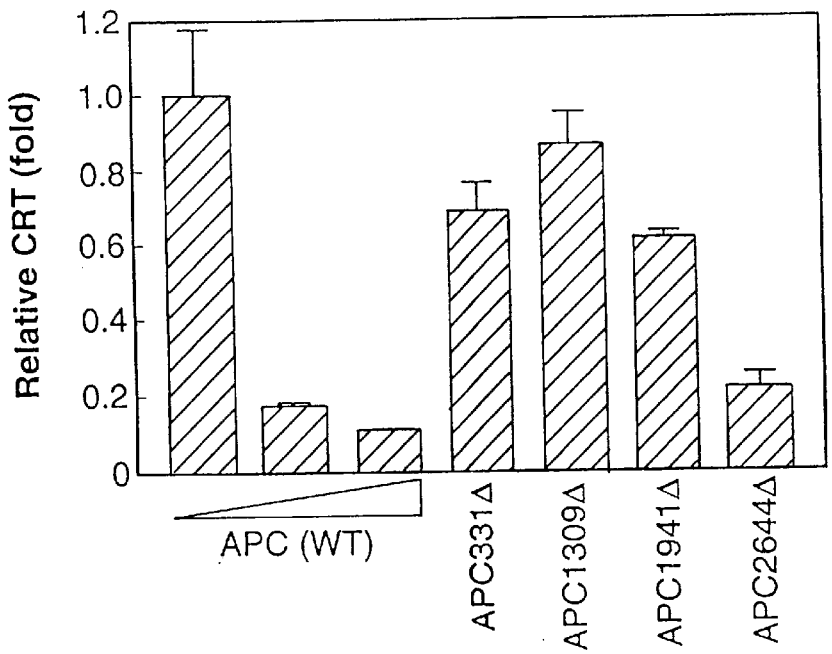
Figure 6B:
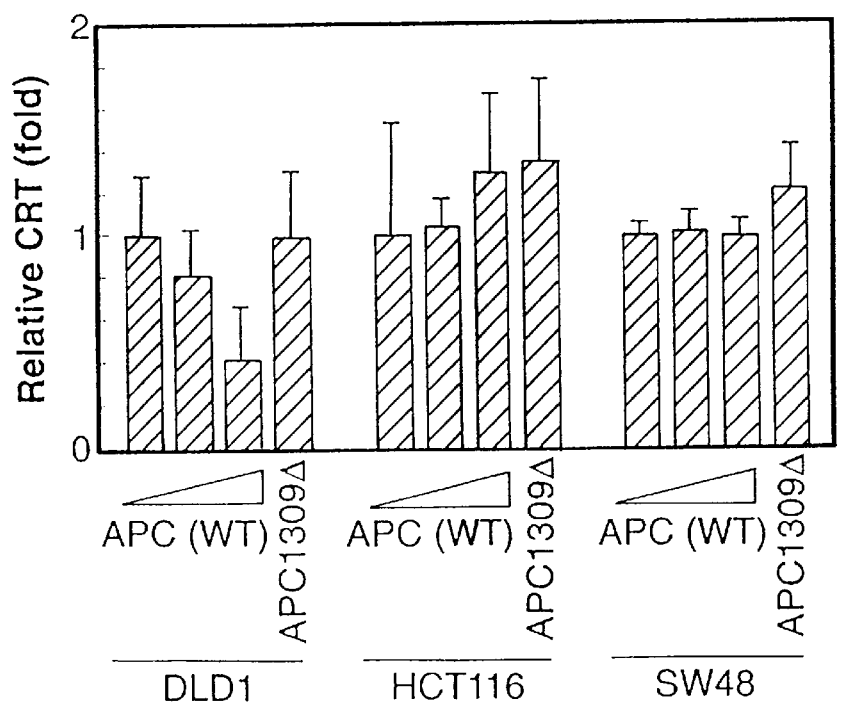
Figure 6A:
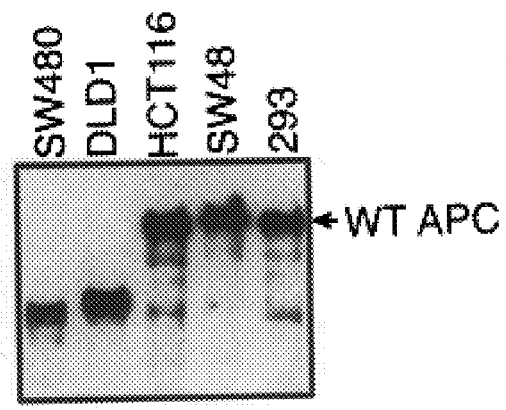

FIGS. 6A and 6B. Evaluation of CRT in colorectal cancer cell lines with WT APC. (FIG. 6A) Inmunoblot of endogenous APC in the DLD1, SW480, HCT116, SW48 and 293 cell lines, developed with APC monoclonal antibody FE9 (34). (FIG. 6B) Effects of exogenous WT APC on CRT in cell lines with endogenous mutated or WT APC. Cells were transfected with increasing amounts (0, 0.15 μg, 0.5 μg for DLD1 and SW48; 0, 0.5 μg, 5 μg for HCT116) of WT APC or APC1309Δ mutant (0.5 μg for DLD1 and SW48; 5 μg for HCT116) and CRT was assessed as in FIG. 5. CRT reporter activities are expressed relative to activity in extracts without exogenous APC and are the means of three replicates. Error bars represent standard deviations.

Figure 7A:
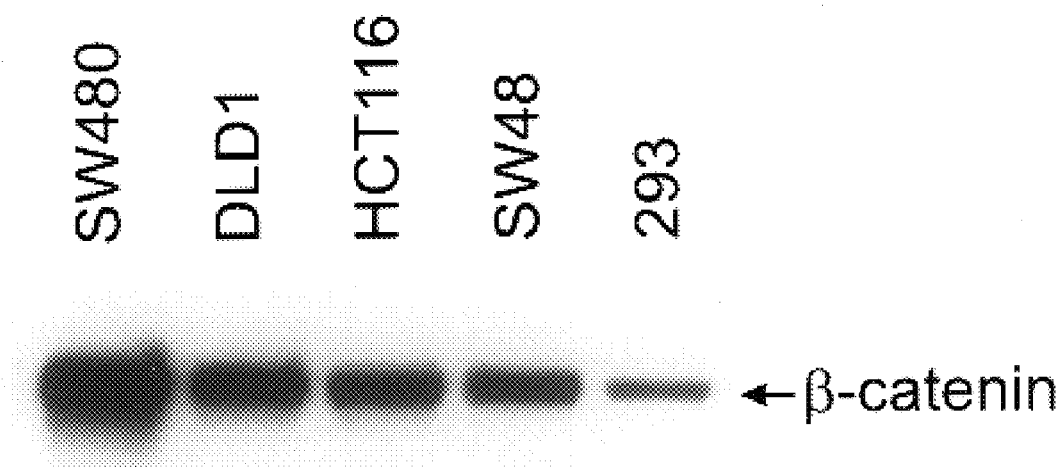
Figure 7B:
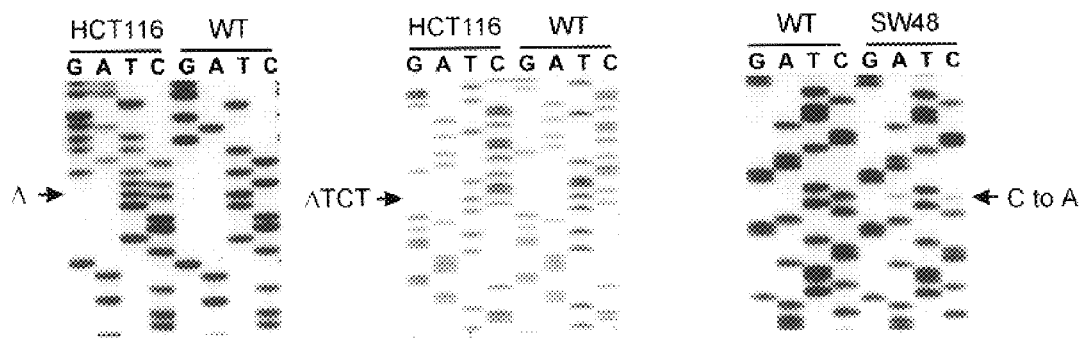
Figure 7C:
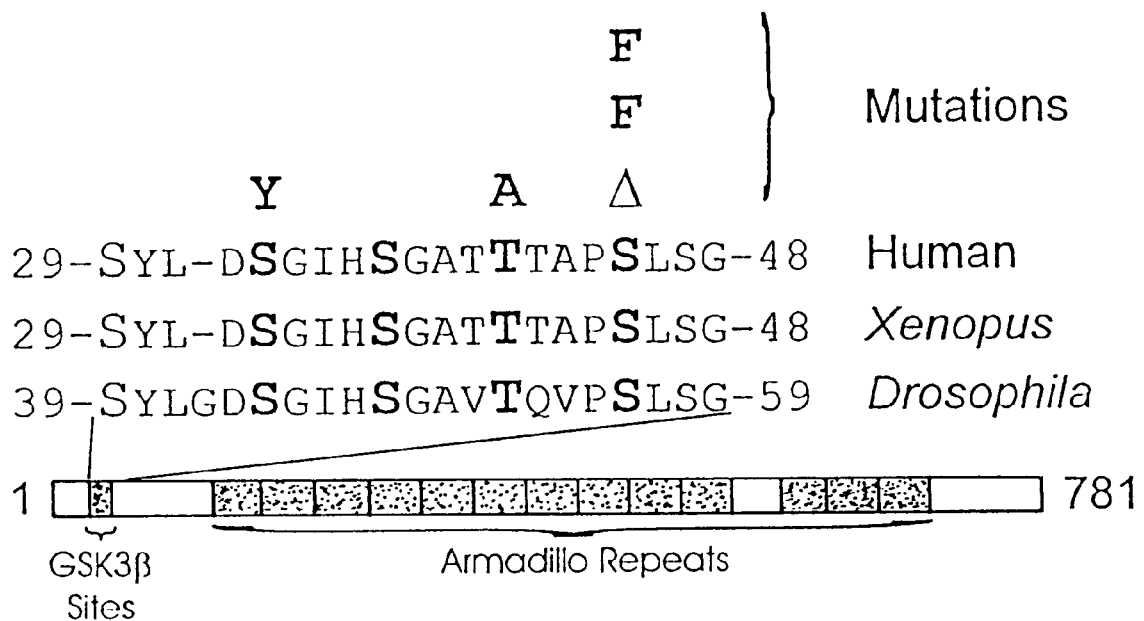

FIGS. 7A, 7B, and 7C. Evaluation of β-catenin in colorectal cancer cell lines with WT APC. (FIG. 7A) Immunoblot of the cell lines used in this study, developed with β-catenin monoclonal C19220 (Transduction Laboratories, Lexington, Ky.)(31). (FIG. 7B) Sequence of CTNNB1 in HCT116 and SW48. Overlapping segments constituting the entire CTNNB1 were amplified by RT-PCR from SW480, DLD1, HCT116, and SW48 cells, and sequenced directly with ThermoSequenase (Amersham). In the case of HCT116, a PCR product containing the deleted region was also cloned into pCI-neo (Promega, Madison) and multiple clones corresponding to each allele were individually sequenced.

The left panel (nts 121 to 143 from HCT116) reveals the presence of a deletion in addition to the WT sequence. The middle panel (antisense strand 156 to 113 of the WT and deleted alleles of HCT116) reveals the 3-bp deletion (ΔTCT)

that removed codon 45 in half the clones. The right panel (nts 80 to 113 from SW48) reveals a C to A transition affecting codon 33 (TCT to TAT). (FIG. 7C) Schematic of β-catenin illustrating the armadillo repeats (33) in human (SEQ ID NO: 10), Xenopus (SEQ ID NO: 10), and Drosophila (SEQ ID NO: 11) and negative regulatory domain. The residues in larger type fit the consensus sequence for GSK3β, phosphorylation (29) and those in bold have been demonstrated to affect down regulation of β-catenin through GSK3β phosphorylation in Xenopus embryos (27). The five mutations found in human colon cancers are indicated at the top.

Figure 8A:
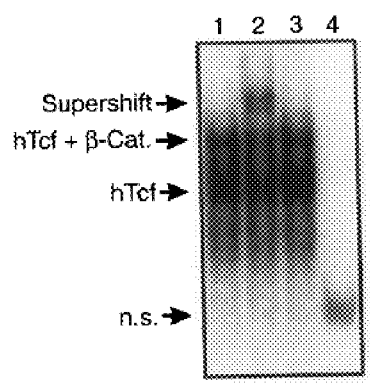
Figure 8B:
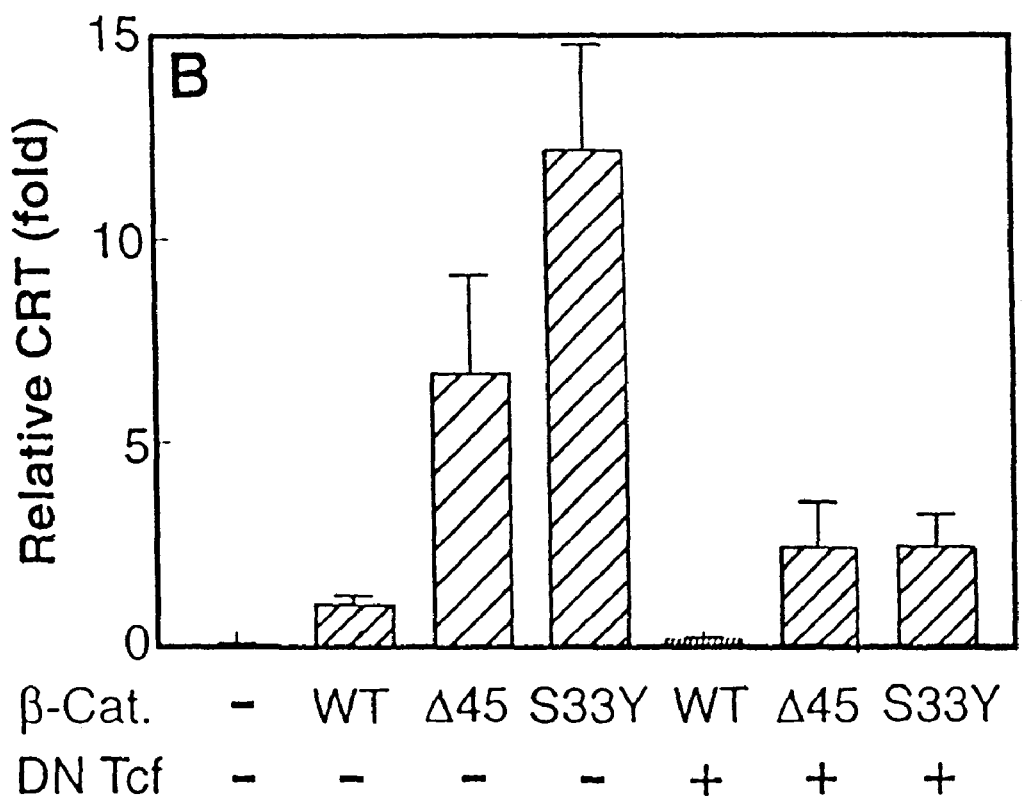

FIGS. 8A and 8B. Functional evaluation of β-catenin mutants. (FIG. 8A) Constitutive nuclear complex of β-catenin and Tcf in HCT116 cells. The presence of nuclear β-catenin-Tcf complexes was assessed by gel shift assays. Lanes 1 to 3, optimal Tcf retardation probe shifted with nuclear extract from HCT116 cells with addition of no antibody (lane 1), anti β-catenin (0.25 μg, lane 2), or an irrelevant antibody (0.25 μg, lane 3). Lane 4, mutant Tcf retardation probe shifted with nuclear extract from HCT116 cells. n.s., nonspecific shifting seen with the mutant probe. (FIG. 8B) Effects of the β-catenin mutations on CRT. 293 cells were transfected with WT (WT) or mutant (Δ45, S33Y) β-catenin and CRT was assessed. CRT reporter activities are expressed relative to WT β-catenin and are the means of three replicates. Error bars represent standard deviations. β-catenin expression constructs were prepared as follows. WT CTNNB1 was amplified by RT-PCR from SW480 cells and cloned into the mammalian expression vector pCI-neo (Promega) to produce pCI-neo-β-cat. The pCI-neo-β-cat Δ45 and S33Y were generated by replacing codons 1 to 89 in pCI-neo-β-cat with a PCR product encoding the equivalent region from HCT116 or SW48 cDNA, respectively. The structures of all constructs were verified by sequence analysis. Lipofectamine was used to cotransfect 293 cells with an internal control (0.1 μg CMV-βgal), a reporter (0.5 μg pTOPFLASH or pFOPFLASH), a Tcf-4 expression vector (0.5 μg pCDNA-TCF4), and β-catenin (0.5 μg) or dominant negative hTcf4 1.0 μg) expression vectors. CRT was determined as described above.

Figure 9A:
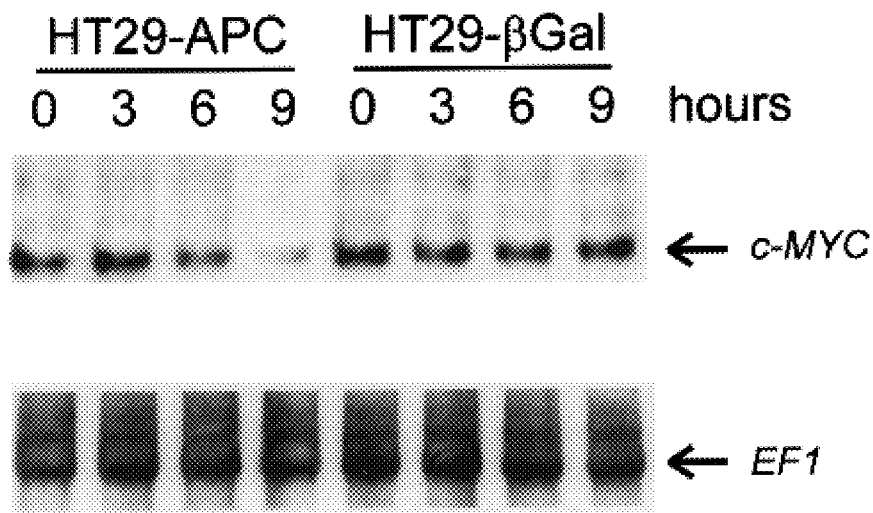
Figure 9B:
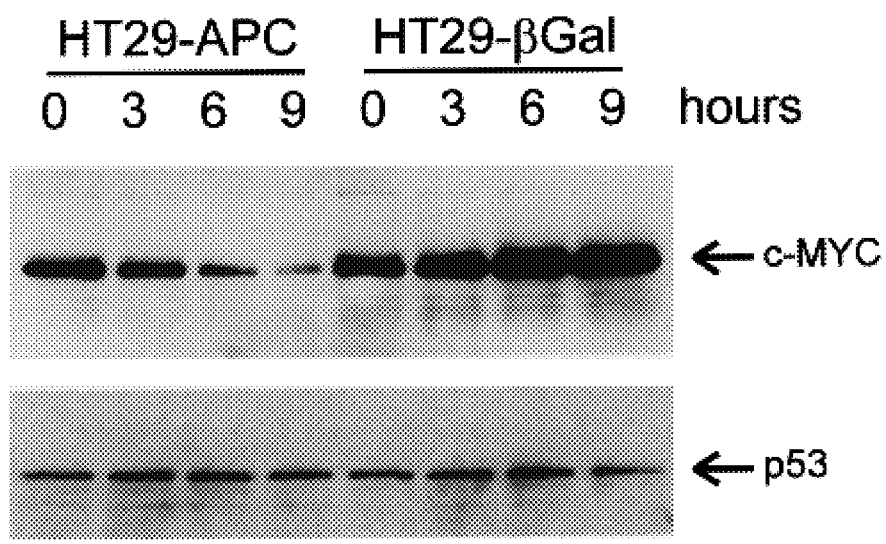

FIGS. 9A and 9B. c-MYC expression after APC induction. (FIG. 9A) Total RNA was isolated from the $ZnCl_2$-treated cells at the indicated times and evaluated on Northern blots (10 μg RNA/lane) that were hybridized with a probe for c-MYC or a control probe for elongation factor 1α mRNA (EF1). (FIG. 9B) Total cellular proteins from the same cells were separated by SDS-polyacrylamide gel electrophoresis and subjected to immunoblotting with a monoclonal antibody to c-MYC (9E10, Santa Cruz Biotechnology). An identical blot probed with a monoclonal antibody to p53 shows that equal amounts of protein were loaded in each lane.

FIGS. 10A–10D. APC- and β-catenin responsive regions within the c-MYC promoter. (FIG. 10A) Map of the c-MYC promoter showing the restriction sites used for generating nested deletions ("Del" constructs) and fragments ("Frag" constructs). The horizontal lines represent the sequences in each reporter construct, which were placed upstream of a minimal promoter and luciferase cassette. P1 and P2 are start sites of transcription; P2 is the major start site. (FIG. 10B) and (FIG. 10C) SW480 cells were cotransfected with the indicated reporter plasmids plus an APC expression construct or a control plasmid. The bars represent luciferase activity in the cells transfected with APC relative to that in cells transfected with the control plasmid. Luciferase activity was measured in three separate experiments, with the bars and brackets representing means and standard deviations, respectively. The constitutive reporter activity (APC off) of the deletions constructs (Del 1 to Del-4) varied less than two fold ranging from 3520 to 6859 as expressed in arbitrary luciferase light units. The constitutive activity of the Frag-A, -B, -C, -D and -E, were 364, 3050, 1063, 1754 and 976, respectively. (FIG. 10D) 293 cells were cotransfected with the indicated reporters plus a β-catenin expression construct or a control plasmid. The increase in luciferase activity in the β-catenin transfectants compared to the control transfectants is plotted on the y-axis. Bars and brackets represent means and standard deviations determined from three separate transfections.

FIGS. 11A–11D. Tcf-4 Binding Elements (TBE) within the c-MYC promoter. (FIG. 11A) Map of the c-MYC promoter, indicating the 2.5-kb region containing the APC- and β-catenin- responsive elements. The fragment containing the wt sequence of the promoter ("TBE1/2") contains TBE sites near both ends. This fragment was engineered to contain mutations in either site 1 (TBE1m/2) or site 2 (TBE1/2m) or both sites 1 and 2 (TBE1m/2m), and each fragment was placed upstream of a minimal promoter and luciferase reporter. Reporters containing four copies of TBE1 (4×TBE1) or TBE2 (4×TBE2) or a mutant TBE2 (4×TBE2m), in the absence of any additional genomic sequences, were constructed similarly. (FIG. 11B) SW480 cells were cotransfected with the indicated reporter plasmids plus an APC expression construct or a control plasmid. Data are presented as in FIG. 2B. (FIG. 11C) 293 cells were cotransfected with the indicated reporters plus a β-catenin expression construct or a control plasmid. The increase in luciferase activity in the β-catenin transfectants compared to the control transfectants is plotted on the y-axis. Bars and brackets represent means and standard deviations determined from three separate transfections. (FIG. 11D) Electrophoresis mobility shift assay (EMSA). Oligonucleotides containing TBE1 or TBE2 sequences ("wt") or mutants ("mt") with nt substitutions at critical positions were end-labeled with $\gamma$-$^{32}$P-ATP and incubated with 0.5 μg of a GST-fusion protein containing the DNA-binding domain of Tcf-4. DNA-protein complexes were separated by electrophoresis and detected as "shifts" from the position of free probe. Unlabelled oligonucleotides (250 ng) were used as competitors (Comp.) in some reactions.

Figure 12:
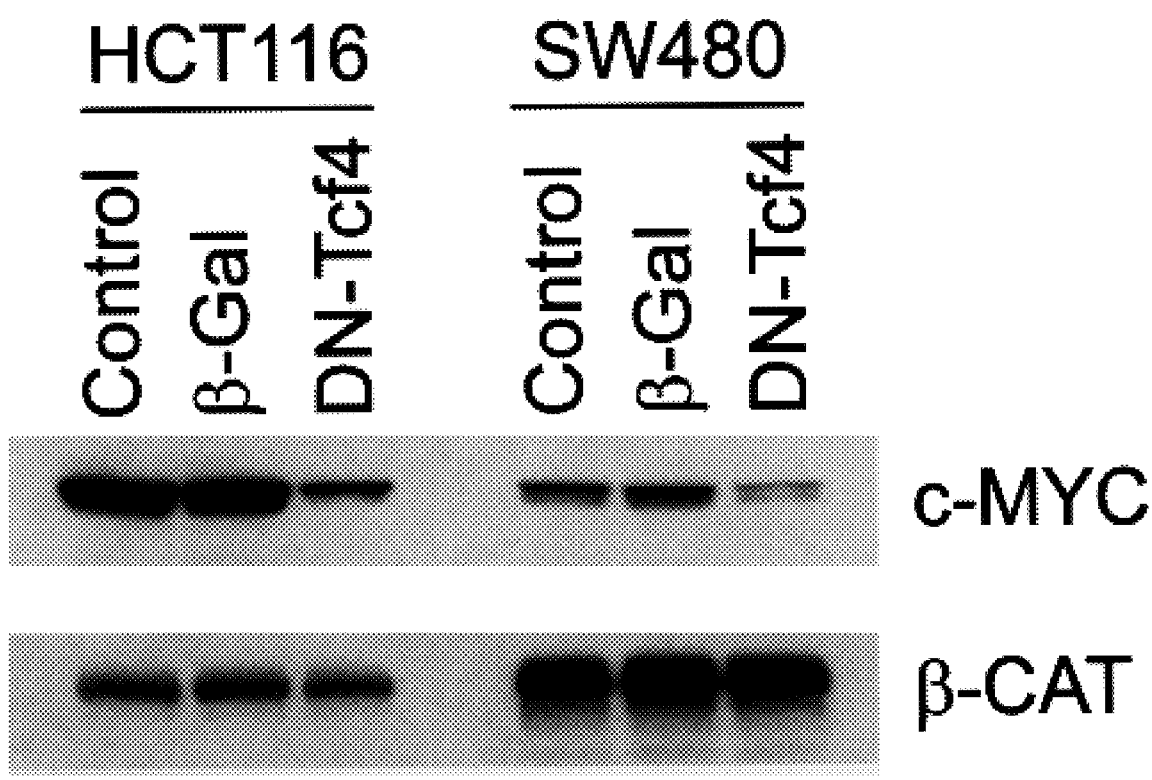

FIG. 12 Repression of c-MYC expression by a dominant-negative Tcf-4. Exponentially growing HCT116 and SW480 cells were mock infected (Control) or infected with adenovirus expressing dominant negative Tcf4 (DN-Tcf4) or β-galactosidase (β-Gal) at multiplicity of infection of 100, respectively. Total cellular proteins were isolated 24 hours after infection and subjected to immunoblotting with a monoclonal antibody to c-MYC (C-19, Santa Cruz Biotechnology). As expected, an identical blot probed with a monoclonal antibody to β-catenin (Transduction Laboratories) shows preservation of the β-catenin protein and that equal amounts of protein were loaded in each lane. The recombinant adenoviruses were constructed using the AdEasy system (25), the details of which are available upon request.

DETAILED DESCRIPTION

It is a discovery of the present invention that hTcf-4 binds to β-catenin and activates transcription in colorectal epithelial cells. Moreover, it has now been found that APC regulates this transcriptional activation, at least in part by binding to β-catenin. In colorectal cancer cells this regulation is frequently abrogated, either by mutation of APC or by mutation of β-catenin.

Two alternative splice forms of human Tcf-4 have been found. One form (hTcf-4E) is homologous to hTcf-1E and the other (hTcf-4B) is homologous to hTcf-1B. The sequence of the nucleotide and amino acid sequences are shown in SEQ ID NOS: 1, 2, 5, and 6. The coding sequences and proteins can be used in assays as described below. Intron-free DNA molecules are provided which are originally made by reverse transcription of a mRNA molecule. They can be propagated in cells or amplified as is desired. Isolated Tcf-4 proteins can be provided substantially free of other human proteins if, for example, the nucleotide sequences are expressed in non-human cells. Methods and vectors for achieving such expression are well known in the art. Choice of such expression means is made by the skilled artisan according to the desired usage and convenience.

Cells can be tested to determine if they have a wild-type APC or a wild-type downstream protein in the APC transcription regulatory pathway, called herein the CRT pathway (β-catenin/Tcf-regulated transcription). One protein within the CRT pathway which has been identified as a target of mutations in human cancers is β-catenin (encoded by the CTNNB1 gene). Other parts of the pathway are also likely to be targets. Although the target genes of the CRT pathway have not been identified, they can be readily identified using the system disclosed here. Genes which are differentially transcribed in the presence of wild-type and mutant CTNNB1, for example, can be identified.

Tcf-responsive reporter genes are those constructs which comprise a readily detectable or assayable gene (such as luciferase, β-galactosidase, chloramphenicol acetyltransferase) linked in cis to a Tcf-responsive element. Such responsive elements are known in the art (7) and any such elements can be used. An optimal Tcf motif contains the sequence CCTTTGATC (SEQ ID NO:3). From one to twenty copies, and preferably from three to six copies, of the motif may be used. Mutation of the sequence to CCTTTG-GCC (SEQ ID NO:4) abrogates responsiveness. One particular Tcf motif which can be used is from the 5' upstream region of the c-MYC gene. The binding motifs which have been identified are TBE1 (CTTTGAT), TBE2 (ATCAAAG). Another necessary part of such constructs is a minimal promoter, such as the c-Fos or the Herpes virus thymidine kinase promoter. Transcription of the reporter gene may be performed by any means known in the art, usually by assaying for the activity of the encoded gene, although immunological detection methods can also be used. In addition, transcription can be monitored by measuring the transcribed mRNA directly, typically using oligonucleotide probes.

As shown below, a cell which has a wild-type APC protein will inhibit CRT. However, most mutations in APC render APC unable to inhibit CRT. Similarly, certain mutations in CTNNB1 render β-catenin super-active and/or refractory to the inhibition by APC. Thus measuring Tcf-responsive reporter gene transcription is an indication of the status of APC and CTNNB1. Mutations in both of these genes are associated with cancers and therefore provides diagnostic and prognostic information.

Assays for CRT can be accomplished in vitro or in cells. If the assay is to be accomplished in cells, then a Tcf-responsive reporter gene must be introduced into the cell. Any means for introducing genetic material into cells can be used, including but not limited to infection, transfection, electroporation. If the assay is to be performed in vitro then the components for transcription must be present. These include suitable buffers, RNA polymerase, as well as ribonucleotides. If the protein product is to be assayed, then the components for translation must also be present, such as ribosomes, and amino acids.

These assays can also be used to screen compounds for potential as anti-cancer therapeutic agents. Using either the in vitro or cell form of the assay, test compounds can be introduced to determine whether they are able to mimic the effect of wild-type APC or to convert a mutant APC into a form which is able to inhibit CRT or a mutant β-catenin into a form which is regulatable by APC. In addition, compounds can be tested for the ability to inhibit the binding of β-catenin and Tcf-4, thus mimicking the action of APC. Such a test can be conducted in vitro or in vivo, for example using a two hybrid assay.

A means for diagnosis of cancers is the result of the observation that CTNNB1 mutations are found in tumor cells, especially those which have wild-type APC. Such mutations can be found, inter alia, by sequencing either the gene or the protein found in a sample. Functional assays can also be used, such as whether β-catenin binds to APC or Tcf-4, or whether it is capable of mediating CRT. Sequences can be compared to those found in a normal tissue of a human, especially the same human who provided the sample being tested. Suitable tumors for testing include, but are not limited to those which are associated with FAP. Suitable tumors include colorectal cancer, thyroid cancer, brain cancer, medulloblastoma, desmoid tumor, osteoma, breast cancer, and head and neck cancer. Because APC mutations are so frequent, and because it appears that APC mutations do not occur in the same tumors as CTNNB1 mutations, one can prescreen samples for APC mutations before performing a CTNNB1 determination.

The portion of the APC gene which encodes the β-catenin binding site can be used in a gene therapy format. Suitable techniques are known in the art for administering genes to tumors, and any such technique can be used. Suitable expression vectors are also known in the art and it is within the skill of the artisan to select an appropriate one. Upon expression in a tumor cell of the β-catenin binding portion of APC, β-catenin will be bound and titrated away from binding to Tcf-4, thus preventing unregulated expression of the CRT target genes. Similarly, a polypeptide portion of APC containing the β-catenin binding site can be administered to cells to perform a titration of β-catenin. Techniques for such administration to cells is well known in the art. Cells which are treated with either the polynucleotide or the polypeptide can be used to study the interaction between APC and β-catenin, and for developing drugs which interfere with such binding.

The above disclosure generally describes the present invention. A more complete understanding can be obtained by reference to the following specific examples which are provided herein for purposes of illustration only, and are not intended to limit the scope of the invention.

EXAMPLE 1

This example identifies Tcf-4 as the expressed family member in colorectal epithelial cells and provides the complete sequence of the cloned cDNA.

There are four known members of the Tcf/Lef family in mammals: the lymphoid-specific factors Tcf-I and Lef-1 (7,8), and the less well characterized Tcf-3 and 4(9). We performed a qualitative Reverse Transcriptase-Polymerase Chain Reaction assay for expression of the four Tcf/Lef genes on 43 colon tumor cell lines. While most colon cell lines expressed more than one of the genes, only hTcf-4 mRNA was expressed in essentially all lines.

Figure 2A:
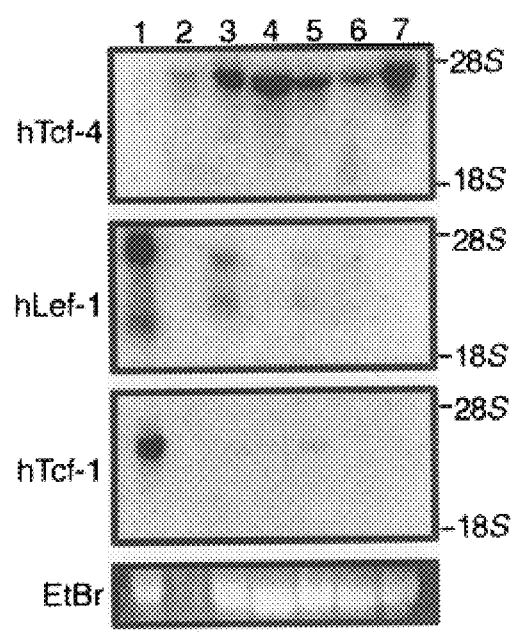
FIGS. 2A, 2B, and 2C. Analysis of hTcf-4 expression in colonic epithelium.
Figure 2B:
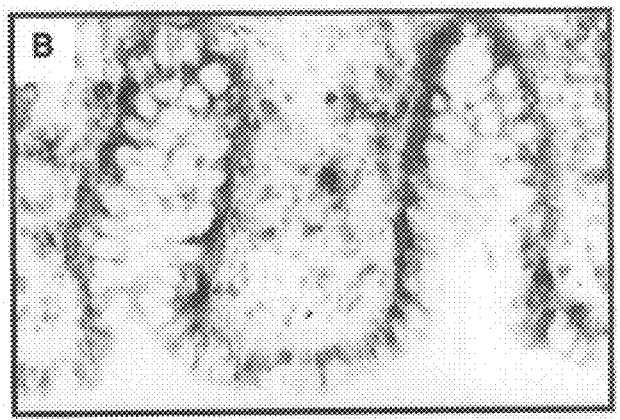

We then screened a human fetal cDNA library and retrieved clones encoding full-length hTcf-4 (FIG. 1). A genomic fragment encoding, the HMG box region of hTcf-4 (7) was used to probe a human 12 week-fetal cDNA library in Lambda GT-11. Positive clones were subcloned into pBluescriptSK and sequenced. See SEQ ID NOS: 1 and 3. The predicted sequence of hTcf-4 was most similar to that of hTcf-1. Alternative splicing yielded two COOH-termini that were conserved between hTcf-1 and hTcf-4. The $NH_2$-terminus, which in hTcf-1, mLef-1 and Xenopus TCF-3 mediates binding to β-catenin (6), was also conserved in hTcf-4. Northern blot analysis of selected colon carcinoma cell lines revealed high-level expression of hTcf-4 (FIG. 2A). Northern blot hybridizations (7) were performed with full-length hTcf-1, hLef-I and hTcf-4 cDNA. Colon epithelial cells were freshly prepared from a mucosal preparation dissected from a healthy surgical colon sample. The sample was minced, and incubated with 1 mM dithiothreitol (DTT) in Hanks' medium to remove mucus. Single-cell suspensions were prepared by incubation at RT in 0.75 mM EDTA in Hanks' medium. Epithelial cells were separated from lymphocytes by Percoll gradient centrifugation.

As evidenced by in situ hybridization (FIGS. 2, B and C) and Northern blotting (FIG. 2A), hTcf-4 mRNA was readily detectable in normal colonic epithelium, whereas hTcf-I and hLef-I were not detectable. In situ hybridization of 6μ frozen sections of healthy colon biopsy samples were performed as described(10). hTcf-4 cDNA encoding amino acids 200 to 310 was amplified and labeled with Dig-11-dUTP (Boehringer Mannheim, Germany) by PCR. After hybridization and washing, the sections were sequentially incubated with mouse anti-Dig antibody (Boehringer) and a horseradish peroxidase conjugated rabbit antibody to mouse immunoglobulin (Dako, Glostrup, Denmark). The signal was visualized with diaminobenzidine, which produces a reddish-brown precipitate. Blue counterstaining was performed with haematoxyline.

EXAMPLE 2

This example demonstrates the interaction of Tcf-4 and β-catenin and their function as a transcriptional activating factor.

To investigate whether hTcf-4 functionally interacts with β-catenin, we used two sets of reporter constructs in a β-catenin-Tcf reporter gene assay (7). One contained three copies of the optimal Tcf motif CCTTTGATC (SEQ ID NO:3), or three copies of the mutant motif CCTTTGGCC (SEQ ID NO:4), upstream of a minimal c-Fos promoter driven-luciferase expression (PTOPFLASH and PFOPFLASH). The second set contained three copies of the optimal motif, or three copies of the mutant motif, upstream of a minimal Herpes virus thymidine kinase promoter driven-Chloramphenicol Acetyl Transferase (CAT) expression (PTOPCAT and PFOPCAT, respectively). Reporter gene assays were performed as in (7). In brief, $2 \times 10^6$ cells were transfected with plasmids by electroporation. After 24 hours, cells were harvested and lysed in 1 mM DTT, 1% Triton X-100, 15% glycerol, 25 mM Tris pH 7.8 and 8 mM $MgCl_2$. cDNAs encoding Myc-tagged versions of β-catenin and hTcf-4 were inserted into the mammalian expression vector pCDNA (Invitrogen). PCATCONTROL, encoding the CAT enzyme under the control of the SV40 promoter, was purchased from Promega.

Epitope-tagged hTcf-4 and a deletion mutant lacking, the $NH_2$-terminal 30 amino acids (ΔNhTcf-4) were cloned into the expression vector pCDNA. Transient transfections were performed in a murine B cell line (IIA1.6), that does not express any of the Tcf genes (6).

Figure 3A:
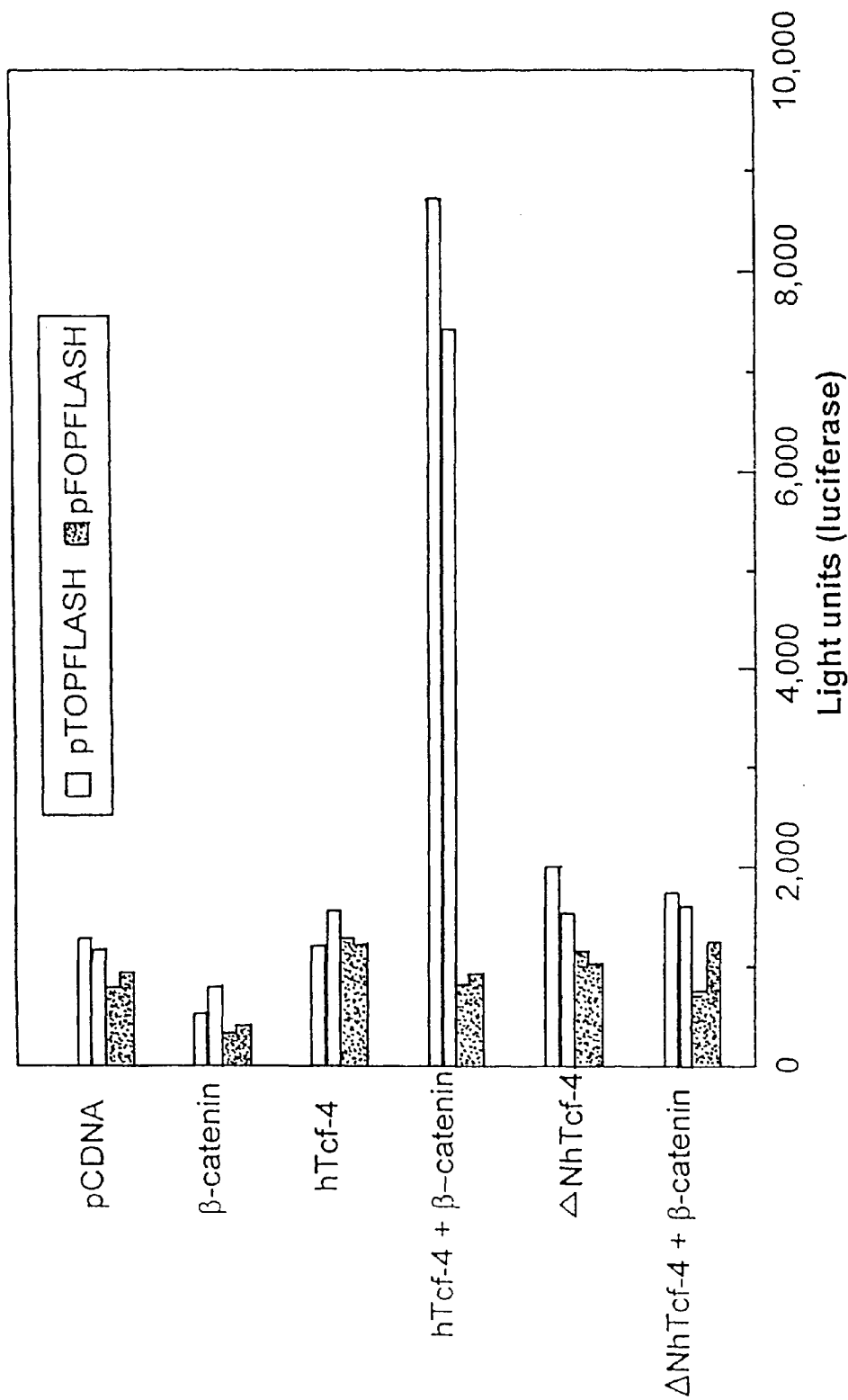

The TOPFLASH reporter was strongly transcribed upon cotransfection with the combination of β-catenin and hTcf-4 plasmids, but not with the individual plasmids or with the combination of β-catenin and ΔNhTcf-4 plasmids. No enhanced transcription was detected in cells transfected with the negative control PFOPFLASH (FIG. 3A). These results show that interaction of the $NH_2$-terminus of hTcf-4 with β-catenin results in transcriptional activation.

EXAMPLE 3

This example demonstrates the functional regulation of CRT transcriptional activation by wild-type APC.

In three $APC^{-/-}$ carcinoma cell lines, SW480, SW620 and DLD-1 (FIG. 3B), the PTOPFLASH reporter was 5–20 fold more actively transcribed than PFOPFLASH. Importantly, transfection of SW480 cells with the reporter gene and an APC-expression vector abrogated the transcriptional activity in a dose-dependent manner (FIG. 3B). In contrast APC had no effect on a cotransfected internal control (pCATCONTROL), or on the basal transcription of PFOPFLASH (FIG. 3B). The use of PTOPCAT and PFOPCAT instead of PTOPFLASH and PFOPFLASH led to comparable observations. The constitutive transcriptional activity of Tcf reporter genes in $APC^{-/-}$ colon carcinoma cells was in stark contrast to the inactivity of these genes in non-colonic cell lines, including IIA1.6 B cells (FIG. 3A), the C57MG breast carcinoma cell line; the Jurkat and BW5147 T cell lines; the Daudi and NS1 B cell lines; the K562 erythromyeloid cell line; the HeLa cervical carcinoma line; the HepG2 hepatoma cell line; 3T3, 3T6, and Rat-I fibroblasts; and the kidney derived SV40-transformed COS cell line (7,16).

EXAMPLE 4

This example demonstrates that a functional β-catenin-hTcf-4 complex exists constitutively in $APC^{-/-}$ cells.

Figure 2C:
Figure 4:
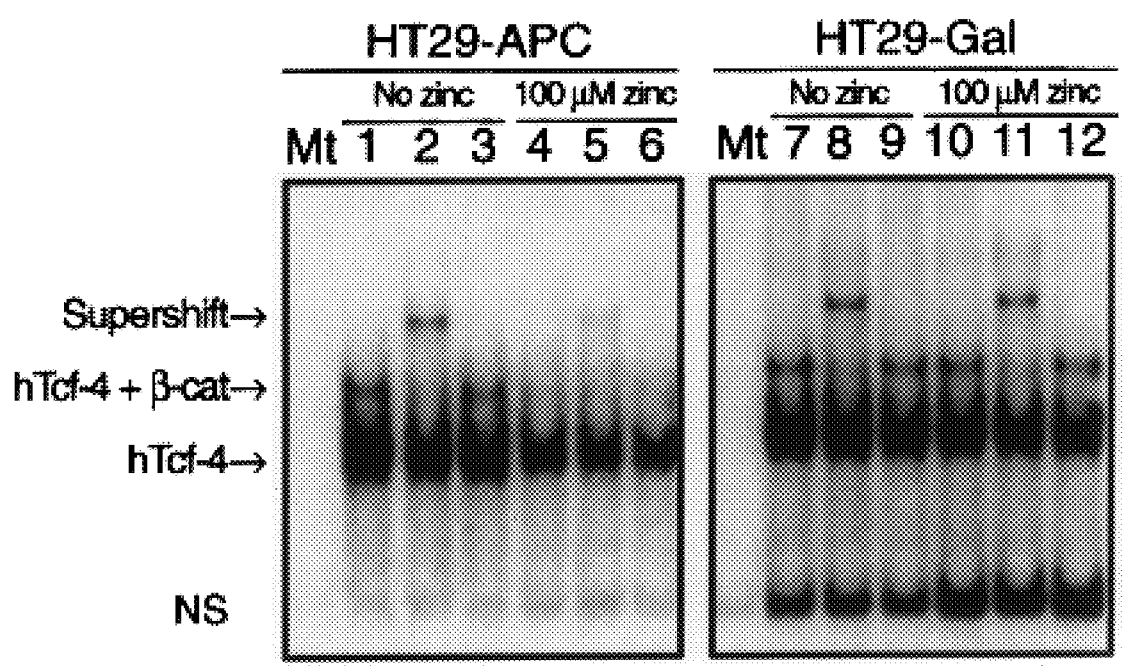
FIG. 4. Constitutive presence of β-catenin-hTcf-4 complexes in APC$^{-/-}$ cells. Gel retardation assays were performed on nuclear extracts from the indicated cell lines before and after a 20-hour exposure to $Zn^{++}$. Samples in lanes 1, 4, 7, 10 were incubated under standard conditions. To the samples in lanes 2, 5, 8, 11, 0.25 μg, anti β-catenin was added. To the samples in lanes 3, 6, 9, 12, 0.25 μg of a control (human CD4) antibody was added. N.S., nonspecific band also observed with mutant (nonbinding) probe (lane Mt).

We used HT29-$APC^{-/-}$ colon carcinoma cells (12), in which APC is controlled by a metallothionein promoter. Induction by $Zn^{++}$ restores wild-type levels of APC, and leads to apoptosis (12). HT29-Gal cells which carry a $Zn^{++}$-inducible LacZ gene were used as a control. The only Tcf family member expressed in HT29 is hTcf-4 (FIG. 2C). In nuclear extracts from uninduced HT29 derived transfectants, we readily detected hTcf-4 by gel retardation (FIG. 4). An additional band of slightly slower mobility was also observed. The addition of a β-catenin antibody resulted in the specific retardation of the latter band, indicating that it represented a β-catenin-hTcf-4 complex (FIG. 4).

(12). After $Zn^{++}$ induction for 20 hours, the β-catenin-hTcf-4 complex was diminished sixfold relative to uncomplexed hTcf-4 in HT29-APC1, while no significant change was observed in HT29-Gal cells (FIG. 4). Importantly, the overall levels of cellular β-catenin do not change during the induction period in HT29-APC1 cells (12).

Gel retardation assays were performed as described elsewhere (7). Extracts were prepared from intact nuclei that were washed four times to avoid contamination with cytoplasmic β-catenin. As the optimal Tcf/Lef probe, we used a double-stranded 15-mer CCCTTTGATCTTACC (SEQ ID NO: 12); the control probe was CCCTTTGGCCTTACC (SEQ ID NO:13). (All oligonudeotides were from Isogene, Holland). The β-catenin antibody was purchased from Transduction Laboratories (Lexington, Ky.). A typical binding reaction contained 3 μg nuclear protein, 0.1 ng radiolabeled probe, 100 ng of dIdC, in 25 μl of binding buffer (60 mm KCl, 1 mM EDTA, 1 mM DTT, 10% glycerol). Samples were incubated for 20 min at room temperature, antibody was added, and the samples incubated 20 min further.

On the basis of these data, we propose the following model. In normal colonic epithelium hTcf-4 is the only expressed member of the Tcf family. The interaction of β-catenin with hTcf-4 is regulated by APC. When appropriate extracellular signals are delivered to an epithelial cell, β-catenin accumulates in a form that is not completed with GSK3β-APC, and that enables its nuclear transport and association with hTcf-4. The HMG domain of hTcf-4 binds in a sequence-specific fashion to the regulatory sequences of specific target genes; β-catenin supplies a transactivation domain. Thus, transcriptional activation of target genes occurs only when hTcf-4 is associated with β-catenin. The hTcf-4 target genes remain to be identified. However, the link with APC and catenin suggests that these genes may participate in the generation and turnover of epithelial cells. Upon loss of wild-type APC, monomeric β-catenin accumulates in the absence of extracellular stimuli, leading to uncontrolled transcription of the hTcf-4 target genes. The apparent de novo expression of other members of the Tcf family in some colon carcinoma cell lines might lead to a further deregulation of Tcf target gene expression by the same mechanism. The control of β-catenin-Tcf signaling is likely to be an important part of the gatekeeper function of APC (19), and its disruption an early step in malignant transformation.

EXAMPLE 5

This example demonstrates that mutant APC protein does not regulate CRT and that a complete set of 20-AA repeats in APC is required to mediate inhibition of CRT.

We tested four APC mutants (FIG. 5A) for their ability to inhibit β-catenin/Tcf-regulated transcription (CRT) in transfection assays. The first mutant, APC331Δ represents a type of mutation found in the germline of Familial Adenomatous Polyposis (FAP) patients as well as in sporadic tumors (15). The APC331Δ protein is truncated at codon 331, amino-terminal to the three 15-amino-acid (AA) β-catenin binding repeats between codons 1020 and 1169. The second mutant, APC1309Δ, is the most common germline APC mutation (15), a 5-bp deletion that produces a frameshift at codon 1309 and truncation of the protein. The APC1309Δ protein retains the 15-AA β-catenin repeats but lacks the seven 20-AA repeats between codons 1323 and 2075 that have been implicated in binding and phosphorylation of β-catenin (18). The third mutant, APC1941Δ, represents one of the most distal somatic mutations observed in colorectal tumors (25). The APC1941Δ protein is truncated at codon 1941 and therefore contains the 15-AA repeats and all but the last two 20-AA repeats. Finally, APC2644Δ represents a germline mutation resulting from a 4-bp deletion in codon 2644. Patients with this type of unusual carboxyl-terminal mutation develop few polyps (attenuated polyposis) but have pronounced extracolonic disease, particularly desmoid tumors (26).

Each of the APC mutants was cotransfected with a CRT reporter into the SW480 colorectal cancer cell line. SW480 cells have truncated APC and constitutively active CRT which can be suppressed by exogenous WT APC. Although all four mutants produced comparable levels of APC protein after transfection, they varied in their CRT inhibitory activity. The three mutants found in patients with typical polyposis or cancer were markedly deficient in inhibition of CRT (FIG. 5B). The reduced activity of APC1309Δ and APC1941Δ suggests that β-catenin binding is not sufficient for APC-mediated inhibition of CRT and that the complete set of 20-AA repeats is required. Interestingly, the inhibitory activity of the APC2644Δ mutant associated with attenuated polyposis was comparable to that of WT APC (FIG. 5B), suggesting that the DLG-binding domain at the carboxyl-terminus of APC is not required for down-regulation of CRT.

WT and mutant APC constructs (2 μg) were transfected into 293, SW480, and HCT116 cells using Lipofectamine (GIBCO/BRL, Gaithersburg). Protein was harvested 24 hours later and subjected to immunoblot analysis with APC monoclonal antibody FE9 (23). In HCT116 and 293 cells, exogenous WT APC comigrated with the endogenous APC. In SW480 cells, APC1309Δ comigrated with the endogenous mutant APC. In all other cases, the nonfunctional APC constructs (APC331Δ, APC 1309Δ, and APC1941Δ) produced as much or more protein than the CRT-functional forms of APC (APC WT and APC 2644Δ).

EXAMPLE 6

This example demonstrates that other components of the APC-regulatory pathway are affected in some cancer cells.

We evaluated CRT in two colorectal tumor cell lines (HCT116 and SW48) that express full-length APC (FIG. 6A). Both HCT116 and SW48 displayed constitutively active CRT and, in contrast to cell lines with truncated APC (DLD1 and SW480), this activity was not inhibited by exogenous WT APC (FIGS. 5B, 6B). Other (noncolorectal cancer) cell lines expressing WT APC do not display constitutive CRT activity. These transfection results suggested that the constitutive CRT in HCT116 and SW48 might be due to an altered downstream component of the APC tumor suppressor pathway.

EXAMPLE 7

This example demonstrates a defect in the gene encoding β-catenin in some cancer cells, which affects CRT.

We evaluated the status of a likely candidate for a downstream component of the APC tumor suppressor pathway, β-catenin, in the same four lines. All four lines expressed similar amounts of apparently intact β-catenin, as assessed by immunoblots (FIG. 7A). However, sequence analysis revealed that both HCT 116 and SW48 harbored mutations in the β-catenin gene (CTNNB1) (FIG. 7B). HCT116 had a 3-bp deletion that removed one AA (Ser-45), and SW48 had a C to A missense mutation that changed Ser-33 to Tyr. Analysis of paraffin-embedded archival tissue from the HCT116 patient confirmed the somatic nature of this mutation and its presence in the primary tumor prior to culture. Interestingly, both mutations affected serines that have been implicated in the downregulation of β-catenin through phosphorylation by the ZW3/GSK3β kinase in Xenopus embryos (FIG. 7C) (27,28).

Genomic DNA was isolated from paraffin-embedded normal and tumor tissue from the patient from whom the HCT116 cell line was derived. A 95 bp PCR product encompassing the mutation was then amplified by PCR and directly sequenced using TERMOSEQUENASE (Amersham). The 3 bp deletion was observed in tumor but not in normal tissue.

To test the generality of this mutational mechanism, we evaluated five primary colorectal cancers in which sequencing of the entire coding region of APC revealed no mutations (25). Three of these five tumors were found to contain CTNNB1 mutations (S45F, S45F, and T44A) that altered potential ZW3/GSK3β phosphorylation sites (FIG. 7C). Each mutation appeared to affect only one of the two CTNNB1 alleles and to be somatic.

Genomic DNA was isolated from frozen-sectioned colorectal cancers and a 1001 bp PCR product containing exon 3 of CTNNB1 was then amplified by PCR and directly sequenced using ThermoSequenase (Amersham). An ACC to GCC change at codon 41 (T41A) and a TCT to TTT at codon 45 (S45F) was observed in one and two tumors, respectively.

EXAMPLE 8

This example demonstrates dominant mutations of CTNNB1 that render CRT insensitive to the effects of WT APC.

Because the β-catenin mutations were heterozygous, we hypothesized that the mutations might exert a dominant effect, rendering a fraction of cellular β-catenin insensitive to APC-mediated down regulation. To test this notion, we performed gel shift analyses with nuclear extracts from untransfected HCT116 cells. In contrast to noncolorectal cancer cell lines with intact APC, HCT116 cells contained a β-catenin/Tcf complex that gel-shifted an optimized Tcf-binding oligonucleotide, and this complex supershifted with anti-β-catenin (FIG. 8A). We also constructed β-catenin expression vectors and compared the biologic activity of the mutant β-catenin from HCT116 ((β-Cat Δ45) and SW48 (β-Cat S33Y) with that of their WT counterpart. For these experiments, we used the 293 kidney epithelial cell line as it is highly transfectable, exhibits low endogenous CRT, and contains a high level of endogenous APC (FIG. 6A). In the presence of endogenous APC, both mutant β-catenins were at least 6-fold more active than the WT protein and this activity was inhibited by dominant-negative hTcf-4 (FIG. 8B).

Together, these results indicate that disruption of APC-mediated regulation of CRT is critical for colorectal tumorigenesis. This is most commonly achieved by recessive inactivating mutations of both APC alleles but, as shown here, can also be achieved by dominant mutations of CTNNB1 that render CRT insensitive to the effects of WT APC. Our results suggest that APC inhibition of CRT requires phosphorylation of β-catenin at multiple sites. These potential phosphorylation sites are consistent with the known specificity of ZW3/GSK3β (29) a serine kinase that negatively regulates β-catenin in Xenopus and Drosophila cells (27) and that interacts with APC and β-catenin in mammalian cells (23). These results also suggest a functional basis for the occasional CTNNB1 mutations observed in other tumor types (30) and illustrate how a critical pathway in human disease can be illuminated by the discovery of mutations in different components of the pathway. The next step in understanding APC function will be the identification of the genes that are activated by hTcf-4/β-catenin complexes and inhibited by WT APC. These genes are likely to be related to APC's ability to induce apoptosis in colorectal cancer cells (31).

REFERENCES
(for preceeding pages)
1. B. Rubinfeld et al *Science,* 262, 1731 (1993); L. K. Su, B. Vogelstein, K. W. Kinzier, ibid 262, 1734 (1993).
2. B. Gumbiner, *Curr. Opin. Cell Biol.* 7, 634 (1995).
3. B. Rubinfeld et al, Science 272, 1023 (1996).
4. J. Papkoff, B. Rubinfeld, B. Schryver, P. Polakis, *Mol. Cell. Biol* 16, 2128 (1996).
5. S. Munemitsa, B. Souza, I. Albert, B. Rubinfeld, P. Polakis, *Proc. Natl. Acad Sci. U.S.A.* 92, 3046 (1995); B. Rubinfeld, B. Souza, I. Albert, S. Muneinitsa, P. Polakis, *J Biol Chem.* 270, 5549 (1995).
6. M. Molenaar et al, *Cell* 86, 396(1996); J. Behrens et al, *Nature* 382, 638 (1996); O. Huber et al, *Mech. Dev.* 59, 3 (1996).
7. M. van de Weterinc, M. Oosterwegel, D. Dooijes, H. Clevers, *EMBO J* 10, 123 (1991); M. van de Wetering, J. Castrop, V. Korinek, *Mol Cell Biol,* 16, 745 (1996).
8. A. Travis et al. *Genes Dev.* 5, 880 (1991); M. L. Waterman, W. H. Fischer, K. A. Jones ibid p. 6562. H. Clevers and R. Grosschedl, *Immunol. Today* 17, 336 (1996).
9. J. Castrop, K. van Norren, H. C. Clevers. *Nucleic Acids Res.* 20, 611 (1992).
10. E. van Hoffen et al, *Am. J Pathol* 149, 1991(1996).
11. M. van de Wetering, M. Oosterwegel, K. van Norren, H. Clevers, EMBO J. 12, 3847 (1993)
12. P. Morin, B. Vogelstein, K. W. Kinzler, *Proc. Natl. Acad. Sci. U.S.A.* 93, 7950 (1996).
13. K. W. Kinzler and B. Vogelstein, *Cell* 87, 159 (1996).
14. About 50% of the Western population develop colorectal adenomas by the age of 70 [D. Ransohoff and C. Lang, *N. Engl. J. Med.* 325, 37 (1991)] and at least 85% of these tumors contain APC mutations; Y. Miyoshi et al., *Hum Mol Genet* 1, 229–33 (1992); J. Jen et al., *Cancer Res.* 54, 5523 (1994).
15. H. Nagase and Y. Nakamura, *Hum. Mutation* 2, 425 (1993).
16. K. W. Kinzler and B. Vogelstein, *Cell* 87, 159 (1996); S. M. Prescott and R. L. White, ibid, p. 783.
17. G. Joslyn, D. S. Richardson, R. White, T. Alber, *Proc. Natl. Acad. Sci. U.S.A.* 90, 11109 (1993); L. K. Su et al., *Cancer Res.* 53, 2728 (1993).
18. B. Rubinfeld et al., *Science* 262, 1731 (1993); L. K. Su, B. Vogelstein, K. W. Kinzler, ibid, p. 1734.
19. J. Hulsken, J. Behrens, W. Birchmeier, *Curr. Opin. Cell. Biol.* 6, 711 (1994); B. Rubinfeld, B. Souza, I. Albert, S. Munemitsu, P. Polakis, *J. Biol. Chem.* 270, 5549 (1995).
20. S. Munemitsu et al., *Cancer Res.* 54, 3676 (1994); K. J. Smith et al., ibid p. 3672.
21. L. K. Su et al., *Cancer Res.* 55, 2972 (1995).
22. A. Matsumine et al., *Science* 272, 1020 (1996).
23. B. Rubinfeld et al., *Science* 272, 1023 (1996).
24. M. Molenaar et al., *Cell* 86, 391 (1996); J. Behrens et al., *Nature* 382, 638 (1996).
25. S. M. Powell et al., *Nature* 359, 235 (1992).
26. D. M. Eccles et al., *Am. J. of Hum. Genet.* 59, 1193 (1996); W. Friedl et al., *Hum Genet* 97, 579 (1996); R. J. Scott et al., *Human Molecular Genetics* 5, 1921 (1996).
27. C. Yost et al., *Genes Dev.* 10, 1443 (1996).
28. S. Munemitsu, I. Albert, B. Rubinfeld, P. Polakis, *Mol Cell Biol* 16, 4088 (1996).
29. M. Peifer, L. M. Pai, M. Casey, *Dev. Biol.* 166, 543 (1994).
30. D J. Kawanishi, et al., *Mol. Cell Biol.* 15, 1175 (1995); P. F. Robbins, et al., *J. Exp. Med.* 183, 1185 (1996).
31. P. J. Morin, B. Vogelstein, K. W. Kinzier, *Proc. Natl. Acad. Sci. U.S.A.* 93, 7950 (1996).
32. J. Groden et al., *Cell* 66,589 (1991); G. Joslyn et al., ibid., p. 601; K. W. Kinzler et al., *Science* 253, 661 (1991); I. Nishisho et al., ibid., p. 665.
33. M. Peifer, S. Berg, A. B. Reynolds, *Cell* 76, 789 (1994).
34. K. J. Smith et al., *Proc. Natl. Acad. Sci. U.S.A.* 90, 2846 (1993).

35. S. E. Goelz, S. R. Hamilton, B. Vogelstein, *Biochem. Biophys. Res. Commun.* 130,118 (1985)

EXAMPLE 9

The adenomatous polyposis coli gene (APC) is a tumor suppressor gene that is inactivated in most colorectal cancers. Mutations of APC cause aberrant accumulation of β-catenin, which then binds T cell factor-4 (Tcf-4), causing increased transcriptional activation of unknown genes. Here, the c-MYC oncogene is identified as a target gene in this signaling pathway. Expression of c-MYC is repressed by wild-type APC and activated by β-catenin, and these effects are mediated through Tcf-4 binding sites in the c-MYC promoter. These results provide a molecular framework for understanding the previously enigmatic overexpression of c-MYC in colorectal cancers.

Most human colorectal tumors are initiated by inactivation of the APC tumor suppressor gene, located on chromosome 5q21 (1). APC is a cytoplasmic protein which can bind to and promote the degradation of β-catenin (2). Among β-catenin functions is the ability to bind members of the Tcf family of transcription factors and activate gene transcription (3). Accordingly, human colorectal tumors with APC or β-catenin mutations exhibit increased β-catenin/Tcf mediated transcription (4, 5). However, the downstream targets of this β-catenin/Tcf-4-regulated transcription are unknown. This study was undertaken to define those targets and thereby gain clues to the mechanisms through which APC affects cellular growth.

To evaluate the transcriptional effects of APC, we studied a human colorectal cancer cell line (H29-APC) containing a zinc-inducible APC gene and a control cell line (HT29-β-Gal) containing an analogous inducible lacZ gene (6). Both endogenous APC alleles in HT29 cells contain truncating mutations, and restoration of wild-type APC expression results in growth inhibition and apoptosis. Upon induction, APC protein is synthesized rapidly and reaches maximal levels by nine hours (7). By twelve hours, a significant fraction of the cells display morphological signs of apoptosis. Because we were interested in identifying changes in gene expression that directly relate to restoration of APC function and not apoptosis, we analyzed the HT29-APC cells nine hours after APC induction.

To evaluate changes in gene expression, we used Serial Analysis of Gene Expression (SAGE), a technique that allows the quantitative evaluation of cellular mRNA in an unbiased manner (8). In brief, the method is based on the use of short sequence tags (15 bp) generated from defined positions within each transcript. Expression levels are deduced from the abundance of individual tags in a sample. SAGE analysis of 51,622 and 55,846 tags from APC-induced and control cells, respectively, allowed identification of 14,346 different transcripts (9), the majority of which were expressed at similar levels in the APC-induced and control cells. Of the 30 tags showing significant differences in expression (10), 14 were overexpressed and 16 were repressed in APC-induced cells. Because biochemical studies have indicated that APC represses β-catenin/Tcf-4-mediated transcription (4,5), we focused on the latter transcripts. One of the three most highly repressed transcripts was a tag corresponding to the c-MYC oncogene (eight tags in HT29-βGal vs. zero in HT29-APC). This repression was confirmed at the mRNA and protein level by Northern blot (FIG. 1A) and immunoblot (FIG. 1B) analysis, respectively. Repression of c-MYC mRNA and protein was evident within 6 hours after zinc induction and within 3 hours after the first detection of APC protein (FIG. 9).

Figure 10A:
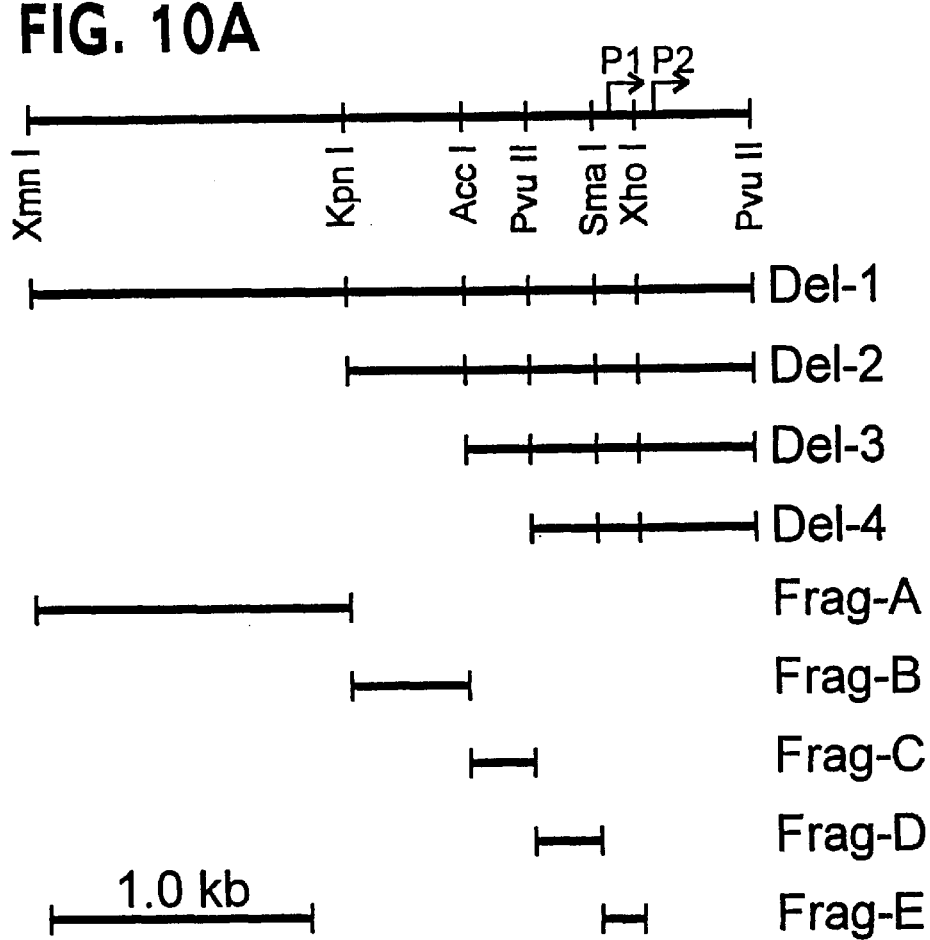
Figure 10B:
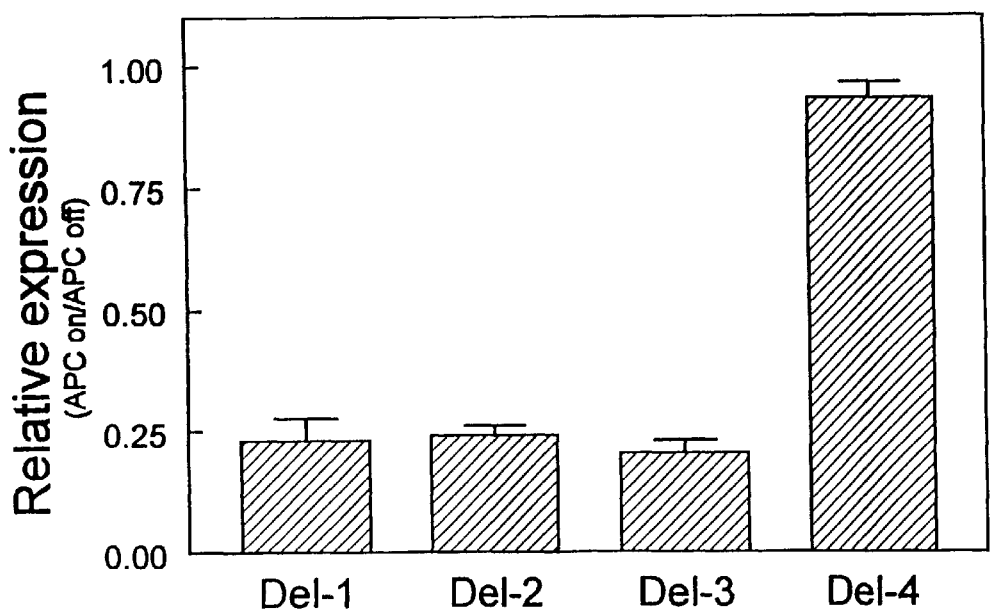
Figure 10C:
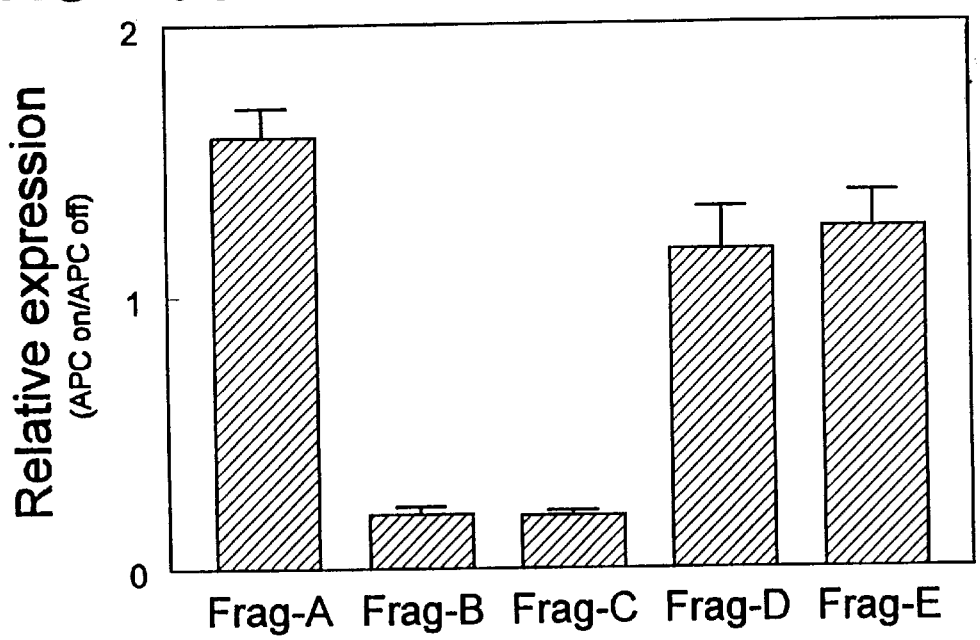
Figure 10D:
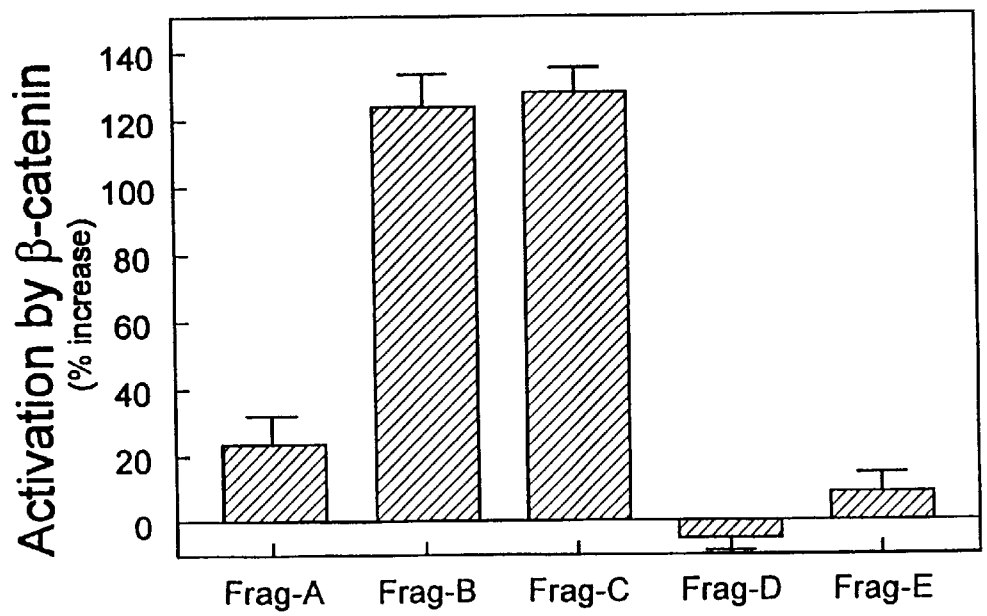
Figure 11A:
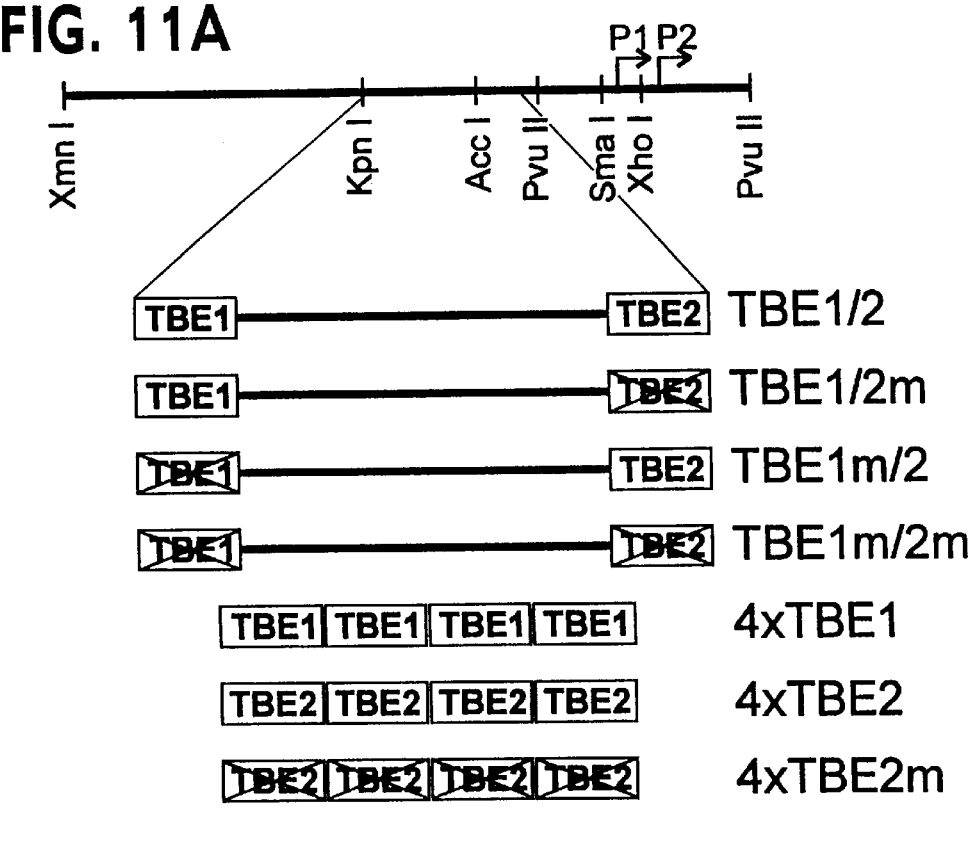
Figure 11B:
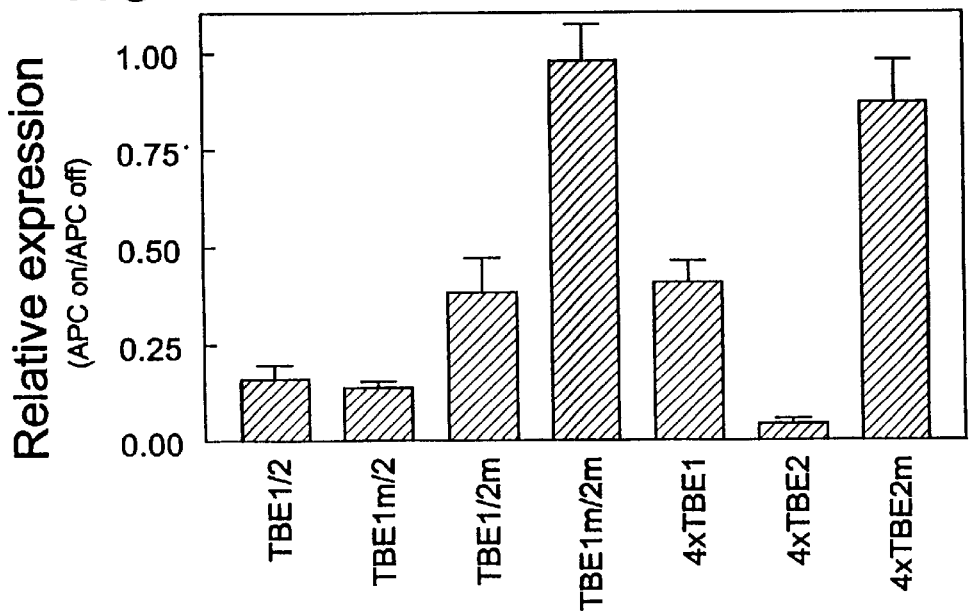
Figure 11C:
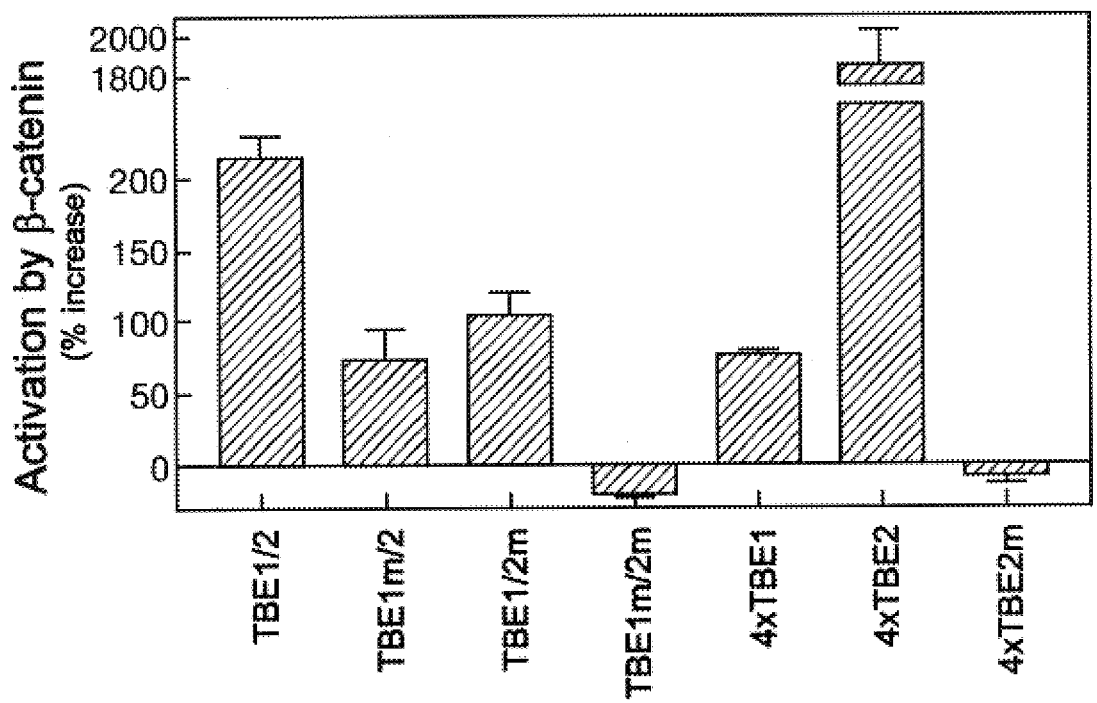

These results suggested that APC might directly modulate c-MYC transcription through β-catenin/Tcf-4. To assess this possibility, we isolated a 2.5-kb genomic fragment encompassing the c-MYC promoter, inserted it upstream of a luciferase reporter gene (11) and then tested the construct for responsiveness to APC (12). This c-MYC promoter region conferred significant transcriptional activity to the basal reporter gene when transfected into human colorectal cancer cells, and this activity was significantly repressed by APC (FIG. 10). Nested deletions of the promoter were used to map the APC-responsive region to a fragment containing nt-1194 to -484 relative to the TATA box at the c-MYC major transcription start site (FIGS. 10A and 10B). Testing of restriction fragments spanning the promoter revealed two responsive regions, one located in fragment B (nt-1194 to -741) and the other in fragment C (nt-741 to -484) (FIG. 11A and FIG. 11C).

If the effects of APC on c-MYC transcription were mediated through inhibition of β-catenin/Tcf-4-regulated transcription, then the c-MYC promoter should be activated by β-catenin. It has previously been shown that β-catenin/Tcf-4 transcription can be activated by exogenous expression of a mutant β-catenin gene in the human kidney cell line 293. The β-catenin construct used for these experiments was mutated at codon 33, rendering it insensitive to downregulation by the endogenous wild-type APC in 293 cells (5). The c-MYC reporter was found to be significantly activated by β-catenin in this line. Using the nested deletion and restriction fragment constructs noted above, we found that the region of the c-MYC promoter that conferred β-catenin responsiveness was the same region (fragments B and C) shown to be APC-repressible in colorectal cancer cells (FIG. 10D).

Analysis of the c-MYC promoter sequence revealed one potential Tcf-4 binding site (13) within fragment B (TBE1) and another within fragment C (TBE2) (FIG. 4A). To test the functional significance of these sites, we created fragments of the c-MYC promoter in which one or both binding sites were eliminated by nucleotide substitutions (14). Mutation of either TBE1 or TBE2 reduced the activity of the c-MYC promoter fragment by 50%. Importantly, deletion of both sites completely removed APC repression and β-catenin activation from the reporter, whereas deletion of either element alone did not abrogate responsiveness (FIGS. 11A to 11C).

Figure 11D:
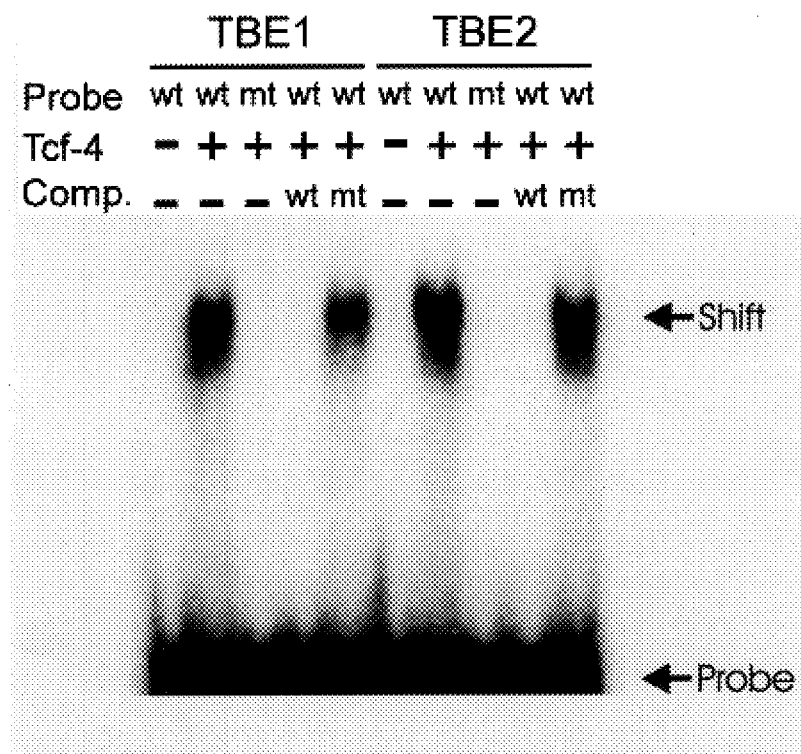

We also tested the TBE1 and TBE2 elements in isolation. Constructs containing four tandem copies of either TBE1 or TBE2 upstream of a minimal promoter (15) conferred β-catenin responsiveness and APC repression to a downstream luciferase reporter (FIGS. 11A to 11C). In all cases, the responsiveness of the reporter containing TBE2 sites was greater than that obtained with TBE1 sites. Nucleotide substitutions within TBE1 or TBE2 that would be expected to abolish Tcf-4 binding abrogated responsiveness to APC and β-catenin (FIGS. 11A to 11C). Finally, to confirm the direct nature of the responsiveness, we tested the ability of Tcf-4 produced in bacteria to bind TBE1 and TBE2 (16). Tcf-4 bound both TBE1 and TBE2, as judged by electrophoresis mobility shift assays, and this binding was abrogated by the same nucleotide substitutions that eliminated transcriptional responses (FIG. 11D).

On the basis of these data, we propose that in normal colorectal epithelial cells, wild-type APC prevents β-catenin from forming a complex with Tcf-4 and activating c-MYC. In colorectal tumors with APC mutations or activating β-catenin mutations, increased β-catenin/Tcf-4 activity leads to overexpression of c-MYC, which then promotes neoplastic growth. Consistent with this model, expression of a dominant negative Tcf-4 in colorectal cancer cells with-mutant β-catenin (HCT116) or mutant APC (SW480) significantly reduced the endogenous levels of c-MYC (FIG. 12). This model is also consistent with c-MYC's powerful oncogenic activities (17) and provides an explanation for two long-standing quandaries. First, it has been extensively documented that c-MYC is overexpressed at the RNA and protein levels at both early and late stages of colorectal tumorigenesis (18). However, unlike the situation in some other cancers, where the c-MYC gene is rearranged or amplified (19), genetic alterations of c-MYC are rare in colorectal tumors and the cause of the overexpression has been unknown (20). The only clue to this mechanism has come from chromosome transfer experiments, in which it was shown that an extra copy of chromosome 5 can repress c-MYC transcription and inhibit neoplastic growth (21). This repression fits well with the molecular data presented here on APC (chromosome 5q21).

The second enigma involves the cyclin-dependent kinase inhibitor p 16INK4a Most tumor types exhibit genetic alterations of the p16INK4a growth-inhibitory pathway, through direct mutation of p16INK4a, its neighbor p15INK4b, or its downstream targets Rb, cdk4, or cyclin D1 (22). Colorectal cancers are a unique and notable exception, in that few mutations of any of the genes in this pathway occur (22,23). The activation of c-MYC through APC inactivation would explain this, as c-MYC expression can bypass p16INK4a- and p15INK4b-mediated growth arrest (24).

REFERENCES AND NOTES

1. J. Groden et al., *Cell* 66, 589 (1991); G. Joslyn et al., ibid., p. 601; K. W. Kinzler et al., *Science* 253, 661 (1991); I. Nishisho et al., ibid., p. 665; K. W. Kinzler and B. Vogelstein, *Cell* 87, 159 (1996).
2. B. Rubinfeld et al., *Science* 262, 1731 (1993); L. K. Su, B. Vogelstein, K. W. Kinzler, *Science* 262, 1734 (1993); S. Munemitsu, I. Albert, B. Souza, B. Rubinfeld, P. Polakis, *Proc. Natl. Acad. Sci. U.S.A.* 92, 3046 (1995); B. Rubinfeld et al., *Science* 275, 1790 (1997).
3 M. Molenaar et al., *Cell* 86, 391 (1996); J. Behrens et al., *Nature* 382, 638 (1996).
4. V. Korinek et al., *Science* 275, 1784 (1997).
5. P. J. Morin et al., ibid. p. 1787.
6. P. J. Morin, B. Vogelstein, K. W. Kinzler, *Proc. Natl. Acad. Sci. U.S.A.* 93, 7950 (1996).
7. Gene expression was induced as in (6) except that 120 µM ZnCl$_2$ was used.
8. V. E. Velculescu, L. Zhang, B. Vogelstein, K. W. Kinzler, *Science* 270, 484 (1995); L. Zhang et al., ibid 276, 1268 (1997); V. E. Velculescu et al., *Cell* 88, 243 (1997).
9. SAGE was performed as in (8) on mRNA from exponentially growing HT29-APC and HT29-βGal cells nine hours after induction. A total of 55,233 and 59,752 tags were obtained from HT29-APC and HT29-βGal cells, respectively. Analysis of internal linker controls revealed a sequencing error rate of 0.065 per tag, corresponding to a sequencing error rate of 0.0067 per base. This was in good agreement with instrument specifications and previous estimates of SAGE tag errors based on analysis of the completed yeast genome (8). After correcting for sequencing mistakes, a total of 107,468 tags representing 51,622 and 55,846 from HT29-APC and HT29-βGal cells, respectively, were analyzed. These tags represented 14,346 unique transcripts, of which 7,811 transcripts appeared at least twice.
10. Expression differences were considered significant if they had a $P_{FALSE}$ of <0.1 as determined by Monte Carlo simulations and they were at least five fold in magnitude (8).
11. A low-basal activity reporter plasmid, pBV-Luc, was first constructed. The pDel-1, pDel-2, pDel-3, pDel4, pFrag-A, pFrag-B, pFrag-C, pFrag-D, and pFrag-E reporters were constructed by cloning corresponding restriction fragments (illustrated in FIG. 2A) of human c-MYC promoter into pBV-Luc. Details of vector construction are available upon request.
12. Exponentially growing SW480 and 293 cells were cultured in 12-well plates and transfected with 0.4 µg reporter, 0.2 µg pCMVβGal control and 0.9 µg effector plasmid using LipofectAmine (Life Technologies, Inc.). The APC [K. J. Smith et al., *Cancer Res.* 54, 3672 (1994)] and β-catenin (5) effector plasmids have been described. Luciferase assays were carried out 24 hours after transfection and normalized for transfection efficiency using β-galactosidase activity. Each assay was performed in triplicate.
13. Two TBE-binding elements were identified in the region conferring APC and β-catenin responsiveness. TBE1 (CTTTGAT) was located 1156 bp upstream of the TATA box at the P1 transcription start site and perfectly matched the consensus for Tcf-binding CTTTG(A/T)(A/T) [M. van de Wetering, M. Oosterwegel, D. Dooijes, H. Clevers, *EMBO J.* 10, 123 (1991); K. Giese, A. Amsterdam, R. Grosschedl, *Genes Dev.* 5, 2567 (1991)]. TBE2 was located 589 bp upstream of the TATA box and contained an inverted perfect match (ATCAAAG). A third Tcf-binding site was located 1400 bp upstream of the TATA box but did not overlap with APC or β-catenin responsiveness.
14. To construct pTBE1/2 plasmid, we used PCR primers (5'-CTAGCTAGCCTAGCACCTTTGATTTCTCCC-3' (SEQ ID NO:15) and 5'-CGTGATATCCGCTlTGATCAA GAGTCCCAG-3' (SEQ ID NO:16)) to amplify nt -576 to -1162 of the c-MYC promoter region. The PCR product was cloned into pBV-Luc. To construct pTBE1/2m, pTBE1m/2, and pTBE1m/2m, we used a mutated TBE1 primer (5'-CTAGCTAGCACTGGTGCATCTCCC AAACCCGGCAGCCCG-3' (SEQ ID NO:17)) and a mutated TBE2 primer (5'-CTGGATATCACTGGT GCATCCCAGGGAGAGTGGAGGAAAG-3' (SEQ ID NO:18)), in combination with either of the wt primers, to amplify the same region, and subcloned the products into pBV-Luc.
15. To construct the four tandem repeats of TBE1, TBE2, and TBE2m, we dimerized oligo cassettes containing two copies of each site and cloned the products into pBV-Luc (for TBE1: 5'-CTAGCGCACCTTTGATTTCTGCAC CTTTGATTTCTG-3' (SEQ ID NO:19) and 5'-CTAGCA GAAATCAAAGGTGCAGAAATCAAAGGTGCG-3' (SEQ ID NO:20); for TBE2: 5'-CTAGCGGACTCT TGATCAAAGGACTCTTGATCAAAG-3' (SEQ ID NO:21) and 5'-CTAGCTTTGATCAAGAGTCCTTTG ATCAAGAGTCCG-3' (SEQ ID NO:22); for TBE2m: 5'-CTAGCGGACTCTTGGCCAAAGGACTCTTGG CCAAAG-3' (SEQ ID NO:23) and 5'-CTAGCTTTGGCC AAGAGTCCTTTGGCCAAGAGTCCG-3' (SEQ ID NO:24).
16. A GST-Tcf-4 fusion protein was constructed by PCR amplification of the sequence encoding the DNA-binding domain (codons 265 to 496) of human Tcf-4 with the following primers: 5'-CGCGGATCCGCTTCCGTGTCC AGGTTCCCTC-3' (SEQ ID NO:25) and 5'-CGGGAA TTCCTAGCCTAGCAGGTTCGGGGAGGG-3' (SEQ ID NO:26). The PCR product was cloned into pGEX-2TK (Pharmacia). GST-Tcf-4 protein was purified from BL-21 cells and DNA-binding assays were performed as described [L. Zawel et al., *Molecular Cell* 1, 611 (1998)]. The probes used for TBE1, TBE2, and TBE2m consisted of the oligonucleotides used for construction of multimerized site reporters (15). For mutant TBE1m, the following primers were used: 5'-CTAGCGCACCTTTGGCTT CTGCACCTTTGGCTTCTG-3' (SEQ ID NO:27) and 5'-CTAGCAGAACGCAAAGGTGCAGAACGCAAA GGTGCG-3'(SEQ ID NO:28). Each binding assay contained 0.5 µg protein and 0.5 ng probe end-labeled to $2 \times 10^8$ dpm/µg. The specificity of binding was tested by competition with unlabeled wt sites and lack of competition with mutant sites.

17. K. B. Marcu, S. A. Bossone, A. J. Patel, *Annu. Rev. Biochem.* 61, 809 (1992); G. J. Kato and C. V. Dang, *FASEB J.* 6, 3065 (1992); B. Amati, K. Alevizopoulos, J. Vlach, *Frontiers in Bioscience* 3, 250 (1998).
18. K. Sikora et al., *Cancer* 59, 1289 (1987); M. D. Erisman, J. K. Scott, R. A. Watt, S. M. Astrin, *Oncogene* 2, 367 (1988); G. G. Finley et al., *Oncogene* 4, 963 (1989); H. Imaseki et al., *Cancer* 64, 704 (1989); D. R. Smith, T. Myint, H. S. Goh, *Br. J. Cancer* 68, 407 (1993).
19. R. Dalla-Favera et al., *Proc. Natl. Acad. Sci. U.S.A.* 79, 7824 (1982); R. Taub et al., ibid., p. 7837; P. Leder et al., *Science* 222, 765 (1983); S. Collins and M. Groudine, *Nature* 298, 679 (1982); R. Dalla-Favera, F. Wong-Staal, R. C. Gallo, *Nature* 299, 61 (1982); C. D. Little, M. M. Nau, D. N. Carney, A. F. Gazdar, J. D. Minna, *Nature* 306, 194 (1983); G. M. Brodeur and M. D. Hogarty, in *The genetic basis of human cancer* K. W. Kinzler and B. Vogelstein, Eds. (McGraw-Hill, New York, 1998), vol. 1, pp. 161–179.
20. M. D. Erisman et al., *Mol. Cell Biol.* 5, 1969 (1985).
21. M. C. Goyette et al., ibid. 12, 1387 (1992); C. Rodriguez-Alfageme, E. J. Stanbridge, S. M. Astrin, *Proc. Natl. Acad. Sci. U.S.A.* 89, 1482 (1992).
22. A. Kamb et al., *Science* 264, 436 (1994); C. J. Sherr, ibid. 274, 1672 (1996); W. R. Sellers and W. G. Kaelin, Jr., *J. Clin. Oncol.* 15, 3301 (1997).
23. J. Jen et al., *Cancer Res.* 54, 6353 (1994); M. Ohhara, M. Esumi, Y. Kuresu, *Biochem. Biophys. Res. Commun.* 226, 791 (1996).
24. K. Alevizopoulos, J. Vlach, S. Hennecke, B. Amati, *EMBO J.* 16, 5322 (1997).
25. T. C. He et al., *Proc. Natl. Acad. Sci. U.S.A.*, 95, 2509 (1998).
26. The authors thank V. Velculescu, L. Zhang, W. Zhou, and K. Polyak for SAGE advice and C. Geltinger for a genomic clone containing the c-MYC promoter. B. V. is an investigator of the Howard Hughes Medical Institute. Supported by NIH grants GM07309 and CA57345. K. W. K. received research funding from Genzyme. Under a licensing agreement between the Johns Hopkins University and Genzyme, SAGE technology is licensed to Genzyme for commercial purposes, and K. W. K and B. V. are entitled to a share of royalty received by the University from sales of the licensed technology. The SAGE technology is freely available to academia for research purposes. K. W. K. and B. V. are consultants to Genzyme. The University and researchers (K. W. K. and B. V.) own Genzyme stock, which is subject to certain restrictions under University policy. The terms of this arrangement are being managed by the University in accordance with its conflict of interest policies. This work is dedicated to the memory of J.-R. He and J.-X. Yang.

SEQUENCE LISTING

```
<160> NUMBER OF SEQ ID NOS: 28

<210> SEQ ID NO 1
<211> LENGTH: 2040
<212> TYPE: DNA
<213> ORGANISM: Homo sapiens

<400> SEQUENCE: 1
atgccgcagc tgaacggcgg tggaggggat gacctaggcg ccaacgacga actgatttcc      60
ttcaaagacg agggcgaaca ggaggagaag agctccgaaa actcctcggc agagagggat     120
ttagctgatg tcaaatcgtc tctagtcaat gaatcagaaa cgaatcaaaa cagctcctcc     180
gattccgagg cggaaagacg gcctccgcct cgctccgaaa gtttccgaga caaatcccgg     240
gaaagtttgg aagaagcggc caagaggcaa gatggagggc tctttaaggg gccaccgtat     300
cccggctacc ccttcatcat gatccccgac ctgacgagcc cctacctccc caagcgatcc     360
gtctcgccca ccgcccgaac ctatctccag atgaaatggc cactgcttga tgtccaggca     420
gggagcctcc agagtagaca agccctcaag gatgccggt ccccatcacc ggcacacatt     480
gtctctaaca aagtgccagt ggtgcagcac cctcaccatg tccaccccct cacgcctctt     540
atcacgtaca gcaatgaaca cttcacgcgc ggaaaccac ctccacactt accagccgac     600
gtagacccca aaacaggaat cccacggcct ccgcaccctc cagatatatc cccgtattac      660
```

-continued

| | |
|---|---|
| ccactatcgc ctggcaccgt aggacaaatc ccccatccgc taggatggtt agtaccacag | 720 |
| caaggtcaac cagtgtaccc aatcacgaca ggaggattca gacacccccta ccccacagct | 780 |
| ctgaccgtca atgcttccgt gtccaggttc cctccccata tggtcccacc acatcatacg | 840 |
| ctacacacga cgggcattcc gcatccggcc atagtcacac caacagtcaa acaggaatcg | 900 |
| tcccagagtg atgtcggctc actccatagt tcaaagcatc aggactccaa aaaggaagaa | 960 |
| gaaaagaaga agccccacat aaagaaacct cttaatgcat tcatgttgta tatgaaggaa | 1020 |
| atgagagcaa aggtcgtagc tgagtgcacg ttgaaagaaa cgcgcggccat caaccagatc | 1080 |
| cttgggcgga ggtggcatgc actgtccaga gaagagcaag cgaaatacta cgagctggcc | 1140 |
| cggaaggagc gacagcttca tatgcaactg taccccggct ggtccgcgcg ggataactat | 1200 |
| ggaaagaaga agaagaggaa aagggacaag cagccggag agaccaatgg agaaaaaaaa | 1260 |
| agtgcgttcg ctacatacaa ggtgaaggca gctgcctcag cccacccctct tcagatggaa | 1320 |
| gcttactaga ttcgcctccc ccctccccga acctgctagg ctcccctccc cgagacgcca | 1380 |
| agtcacagac tgagcagacc cagcctctgt cgctgtccct gaagcccgac cccctggccc | 1440 |
| acctgtccat gatgcctccg ccaccgccc tcctgctcgc tgaggccacc cacaaggcct | 1500 |
| ccgccctctg tcccaacggg gccctggacc tgccccccagc cgctttgcag cctgccgccc | 1560 |
| cctcctcatc aattgcacag ccgtcgactt cttggttaca ttcccacagc tccctggccg | 1620 |
| ggacccagcc ccagccgctg tcgctcgtca ccaagtcttt agaatagctt tagcgtcgtg | 1680 |
| aaccccgctg ctttgtttat ggttttgttt cacttttctt aatttgcccc ccaccccac | 1740 |
| cttgaaaggt tttgttttgt actctcttaa ttttgtgcca tgtggctaca ttagttgatg | 1800 |
| tttatcgagt tcattggtca atatttgacc cattcttatt tcaatttctc cttttaaata | 1860 |
| tgtagatgag agaagaacct catgattggt accaaaattt ttatcaacag ctgtttaaag | 1920 |
| tctttgtagc gtttaaaaaa tatatatata tacataactg ttatgtagtt cggatagctt | 1980 |
| agttttaaaa gactgattaa aaaacaaaaa aaaaaaagc ttgcgaggga tcccccggga | 2040 |

<210> SEQ ID NO 2
<211> LENGTH: 2444
<212> TYPE: DNA
<213> ORGANISM: Homo sapiens

<400> SEQUENCE: 2

| | |
|---|---|
| ggttttttttt ttttaccccc ctttttttatt tattatttttt ttgcacattg agcggatcct | 60 |
| tgggaacgag agaaaaaaga aacccaaact cacgcgtgca gaagatctcc ccccccttcc | 120 |
| cctcccctcc tccctctttt ccctccccca ggagaaaaag accccccaagc agaaaaaagt | 180 |
| tcaccttgga ctcgtctttt tcttgcaata ttttttgggg gggcaaaact ttgagggggt | 240 |
| gatttttttt ggcttttctt cctccttcat ttttcttcca aaattgctgc tggtgggtga | 300 |
| aaaaaaaatg ccgcagctga acggcggtgg aggggatgac ctaggcgcca acgacgaact | 360 |
| gatttccttc aaagacgagg gcgaacagga ggagaagagc tccgaaaact cctcggcaga | 420 |
| gagggattta gctgatgtca aatcgtctct agtcaatgaa tcagaaacga atcaaaacag | 480 |
| ctcctccgat tccgaggcgg aaagacggcc tccgcctcgc tccgaaagtt tccgagacaa | 540 |
| atcccgggaa agtttggaag aagcggccaa gaggcaagat ggagggctct ttaaggggcc | 600 |
| accgtatccc ggctacccct tcatcatgat ccccgacctg acgagcccct acctccccaa | 660 |
| gcgatccgtc tcgcccaccg cccgaaccta tctccagatg aaatggccac tgcttgatgt | 720 |
| ccaggcaggg agcctccaga gtagacaagc cctcaaggat gcccggtccc catcaccggc | 780 |

```
acacattgtc tctaacaaag tgccagtggt gcagcaccct caccatgtcc acccccctcac    840 gcctcttatc acgtacagca atgaacactt cacgccggga aacccacctc cacacttacc    900
agccgacgta gaccccaaaa caggaatccc acggcctccg caccctccag atatatcccc    960
gtattaccca ctatcgcctg gcaccgtagg acaaatcccc catccgctag gatggttagt    1020
accacagcaa ggtcaaccag tgtacccaat cacgacagga ggattcagac accccctaccc   1080 cacagctctg accgtcaatg cttccgtgtc caggttccct ccccatatgg tcccaccaca    1140
tcatacgcta cacgacgg gcattccgca tccggccata gtcacaccaa cagtcaaaca     1200
ggaatcgtcc cagagtgatg tcggctcact ccatagttca aagcatcagg actccaaaaa    1260
ggaagaagaa aagaagaagc cccacataaa gaaacctctt aatgcattca tgttgtatat    1320
gaaggaaatg agagcaaagg tcgtagctga gtgcacgttg aaagaaagcg cggccatcaa    1380
ccagatcctt gggcggaggt ggcatgcact gtccagagaa gagcaagcga aatactacga    1440
gctggcccgg aaggagcgac agcttcatat gcaactgtac cccggctggt ccgcgcggga    1500
taactatgga aagaagaaga agaggaaaag ggacaagcag ccgggagaga ccaatgaaca    1560
cagcgaatgt ttcctaaatc cttgcctttc acttcctccg attacagacc tcagcgctcc    1620
taagaaatgc cgagcgcgct ttggccttga tcaacgaaat aactggtgcg gcccttgcag    1680
gagaaaaaaa aagtgcgttc gctacataca aggtgaaggc agctgcctca gcccacccctc   1740 ttcagatgga agcttactag attcgcctcc cccctcccg aacctgctag gctcccctcc     1800
ccgagacgcc aagtcacaga ctgagcagac ccagcctctg tcgctgtccc tgaagcccga    1860 cccccctggcc cacctgtcca tgatgcctcc gccacccgcc ctcctgctcg ctgaggccac    1920
ccacaaggcc tccgccctct gtcccaacgg ggccctggac ctgcccccag ccgctttgca    1980
gcctgccgcc ccctcctcat caattgcaca gccgtcgact tcttggttac attcccacag    2040
ctccctggcc gggacccagc cccagccgct gtcgctcgtc accaagtctt tagaatagct    2100
ttagcgtcgt gaaccccgct gctttgttta tggttttgtt tcactttttct taatttgccc    2160 cccaccccca ccttgaaagg ttttgttttg tactctctta attttgtgcc atgtggctac    2220
attagttgat gtttatcgag ttcattggtc aatatttgac ccattcttat ttcaatttct    2280 cctttttaaat atgtagatga gagaagaacc tcatgattgg taccaaaatt tttatcaaca   2340
gctgtttaaa gtcttttgtag cgtttaaaaa atatatatat atacataact gttatgtagt   2400
tcggatagct tagtttttaaa agactgatta aaaaacaaaa aaaa                    2444
```

<210> SEQ ID NO 3
<211> LENGTH: 15
<212> TYPE: DNA
<213> ORGANISM: Homo sapiens
<400> SEQUENCE: 3
ccctttgatc ttacc                                                     15

<210> SEQ ID NO 4
<211> LENGTH: 15
<212> TYPE: DNA
<213> ORGANISM: Homo sapiens
<400> SEQUENCE: 4
ccctttggcc ttacc                                                     15

<210> SEQ ID NO 5

```
<211> LENGTH: 442
<212> TYPE: PRT
<213> ORGANISM: Homo sapiens

<400> SEQUENCE: 5

Met Pro Gln Leu Asn Gly Gly Gly Asp Leu Gly Ala Asn Asp
1               5                   10                  15

Glu Leu Ile Ser Phe Lys Asp Glu Gly Glu Gln Glu Glu Lys Ser Ser
            20                  25                  30

Glu Asn Ser Ser Ala Glu Arg Asp Leu Ala Asp Val Lys Ser Ser Leu
        35                  40                  45

Val Asn Glu Ser Glu Thr Asn Gln Asn Ser Ser Ser Asp Ser Glu Ala
    50                  55                  60

Glu Arg Arg Pro Pro Arg Ser Glu Ser Phe Arg Asp Lys Ser Arg
65                  70                  75                  80

Glu Ser Leu Glu Glu Ala Ala Lys Arg Gln Asp Gly Gly Leu Phe Lys
                85                  90                  95

Gly Pro Pro Tyr Pro Gly Tyr Pro Phe Ile Met Ile Pro Asp Leu Thr
            100                 105                 110

Ser Pro Tyr Leu Pro Lys Arg Ser Val Ser Pro Thr Ala Arg Thr Tyr
        115                 120                 125

Leu Gln Met Lys Trp Pro Leu Leu Asp Val Gln Ala Gly Ser Leu Gln
    130                 135                 140

Ser Arg Gln Ala Leu Lys Asp Ala Arg Ser Pro Ser Pro Ala His Ile
145                 150                 155                 160

Val Ser Asn Lys Val Pro Val Val Gln His Pro His His Val His Pro
                165                 170                 175

Leu Thr Pro Leu Ile Thr Tyr Ser Asn Glu His Phe Thr Pro Gly Asn
            180                 185                 190

Pro Pro Pro His Leu Pro Ala Asp Val Asp Pro Lys Thr Gly Ile Pro
        195                 200                 205

Arg Pro Pro His Pro Pro Asp Ile Ser Pro Tyr Tyr Pro Leu Ser Pro
    210                 215                 220

Gly Thr Val Gly Gln Ile Pro His Pro Leu Gly Trp Leu Val Pro Gln
225                 230                 235                 240

Gln Gly Gln Pro Val Tyr Pro Ile Thr Thr Gly Gly Phe Arg His Pro
                245                 250                 255

Tyr Pro Thr Ala Leu Thr Val Asn Ala Ser Val Ser Arg Phe Pro Pro
            260                 265                 270

His Met Val Pro Pro His His Thr Leu His Thr Thr Gly Ile Pro His
        275                 280                 285

Pro Ala Ile Val Thr Pro Thr Val Lys Gln Glu Ser Ser Gln Ser Asp
    290                 295                 300

Val Gly Ser Leu His Ser Ser Lys His Gln Asp Ser Lys Lys Glu Glu
305                 310                 315                 320

Glu Lys Lys Lys Pro His Ile Lys Lys Pro Leu Asn Ala Phe Met Leu
                325                 330                 335

Tyr Met Lys Glu Met Arg Ala Lys Val Val Ala Glu Cys Thr Leu Lys
            340                 345                 350

Glu Ser Ala Ala Ile Asn Gln Ile Leu Gly Arg Arg Trp His Ala Leu
        355                 360                 365

Ser Arg Glu Glu Gln Ala Lys Tyr Tyr Glu Leu Ala Arg Lys Glu Arg
    370                 375                 380

Gln Leu His Met Gln Leu Tyr Pro Gly Trp Ser Ala Arg Asp Asn Tyr
```

-continued

```
           385                  390                 395                 400
Gly Lys Lys Lys Arg Lys Arg Asp Lys Gln Pro Gly Glu Thr Asn
                    405                 410                 415
Gly Glu Lys Lys Ser Ala Phe Ala Thr Tyr Lys Val Lys Ala Ala Ala
                420                 425                 430
Ser Ala His Pro Leu Gln Met Glu Ala Tyr
            435                 440

<210> SEQ ID NO 6
<211> LENGTH: 596
<212> TYPE: PRT
<213> ORGANISM: Homo sapiens

<400> SEQUENCE: 6

Met Pro Gln Leu Asn Gly Gly Gly Asp Leu Gly Ala Asn Asp
  1               5                  10                  15
Glu Leu Ile Ser Phe Lys Asp Glu Gly Glu Gln Glu Glu Lys Ser Ser
                 20                  25                  30
Glu Asn Ser Ser Ala Glu Arg Asp Leu Ala Asp Val Lys Ser Ser Leu
             35                  40                  45
Val Asn Glu Ser Glu Thr Asn Gln Asn Ser Ser Ser Asp Ser Glu Ala
 50                  55                  60
Glu Arg Arg Pro Pro Arg Ser Glu Ser Phe Arg Asp Lys Ser Arg
 65                  70                  75                  80
Glu Ser Leu Glu Glu Ala Ala Lys Arg Gln Asp Gly Gly Leu Phe Lys
                 85                  90                  95
Gly Pro Pro Tyr Pro Gly Tyr Pro Phe Ile Met Ile Pro Asp Leu Thr
            100                 105                 110
Ser Pro Tyr Leu Pro Asn Gly Ser Val Ser Pro Thr Ala Arg Thr Tyr
            115                 120                 125
Leu Gln Met Lys Trp Pro Leu Leu Asp Val Gln Ala Gly Ser Leu Gln
            130                 135                 140
Ser Arg Gln Ala Leu Lys Asp Ala Arg Ser Pro Ser Pro Ala His Ile
145                 150                 155                 160
Val Ser Asn Lys Val Pro Val Val Gln His Pro His His Val His Pro
                165                 170                 175
Leu Thr Pro Leu Ile Thr Tyr Ser Asn Glu His Phe Thr Pro Gly Asn
            180                 185                 190
Pro Pro Pro His Leu Pro Ala Asp Val Asp Pro Lys Thr Gly Ile Pro
            195                 200                 205
Arg Pro Pro His Pro Pro Asp Ile Ser Pro Tyr Tyr Pro Leu Ser Pro
        210                 215                 220
Gly Thr Val Gly Gln Ile Pro His Pro Leu Gly Trp Leu Val Pro Gln
225                 230                 235                 240
Gln Gly Gln Pro Val Tyr Pro Ile Thr Thr Gly Gly Phe Arg His Pro
                245                 250                 255
Tyr Pro Thr Ala Leu Thr Val Asn Ala Ser Val Ser Arg Phe Pro Pro
            260                 265                 270
His Met Val Pro Pro His His Thr Leu His Thr Thr Gly Ile Pro His
        275                 280                 285
Pro Ala Ile Val Thr Pro Thr Val Lys Gln Glu Ser Ser Gln Ser Asp
        290                 295                 300
Val Gly Ser Leu His Ser Ser Lys His Gln Asp Ser Lys Lys Glu Glu
305                 310                 315                 320
```

-continued

```
Glu Lys Lys Lys Pro His Ile Lys Lys Pro Leu Asn Ala Phe Met Leu
                325                 330                 335

Tyr Met Lys Glu Met Arg Ala Lys Val Val Ala Glu Cys Thr Leu Lys
            340                 345                 350

Glu Ser Ala Ala Ile Asn Gln Ile Leu Gly Arg Arg Trp His Ala Leu
        355                 360                 365

Ser Arg Glu Glu Gln Ala Lys Tyr Tyr Glu Leu Ala Arg Lys Glu Arg
    370                 375                 380

Gln Leu His Met Gln Leu Tyr Pro Gly Trp Ser Ala Arg Asp Asn Tyr
385                 390                 395                 400

Gly Lys Lys Lys Arg Lys Arg Asp Lys Gln Pro Gly Glu Thr Asn
                405                 410                 415

Glu His Ser Glu Cys Phe Leu Asn Pro Cys Leu Ser Leu Pro Pro Ile
            420                 425                 430

Thr Asp Leu Ser Ala Pro Lys Lys Cys Arg Ala Arg Phe Gly Leu Asp
        435                 440                 445

Gln Gln Asn Asn Trp Cys Gly Pro Cys Arg Arg Lys Lys Lys Cys Val
    450                 455                 460

Arg Tyr Ile Gln Gly Glu Gly Ser Cys Leu Ser Pro Pro Ser Ser Asp
465                 470                 475                 480

Gly Ser Leu Leu Asp Ser Pro Pro Ser Pro Asn Leu Leu Gly Ser
                485                 490                 495

Pro Pro Arg Asp Ala Lys Ser Gln Thr Glu Gln Thr Gln Pro Leu Ser
            500                 505                 510

Leu Ser Leu Lys Pro Asp Pro Leu Ala His Leu Ser Met Met Pro Pro
        515                 520                 525

Pro Pro Ala Leu Leu Leu Ala Glu Ala Thr His Lys Ala Ser Ala Leu
    530                 535                 540

Cys Pro Asn Gly Ala Leu Asp Leu Pro Pro Ala Ala Leu Gln Pro Ala
545                 550                 555                 560

Ala Pro Ser Ser Ser Ile Ala Gln Pro Ser Thr Ser Trp Leu His Ser
                565                 570                 575

His Ser Ser Leu Ala Gly Thr Gln Pro Gln Pro Leu Ser Leu Val Thr
            580                 585                 590

Lys Ser Leu Glu
        595

<210> SEQ ID NO 7
<211> LENGTH: 2973
<212> TYPE: PRT
<213> ORGANISM: Homo sapiens

<400> SEQUENCE: 7

Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95
```

-continued

```
Gly Ser Arg Glu Gly Ser Val Ser Arg Ser Gly Glu Cys Ser Pro
            100                 105                 110
Val Pro Met Gly Ser Phe Pro Arg Arg Gly Phe Val Asn Gly Ser Arg
            115                 120                 125
Glu Ser Thr Gly Tyr Leu Glu Glu Leu Glu Lys Glu Arg Ser Leu Leu
            130                 135                 140
Leu Ala Asp Leu Asp Lys Glu Glu Lys Glu Lys Asp Trp Tyr Tyr Ala
145                 150                 155                 160
Gln Leu Gln Asn Leu Thr Lys Arg Ile Asp Ser Leu Pro Leu Thr Glu
                165                 170                 175
Asn Phe Ser Leu Gln Thr Asp Met Thr Arg Arg Gln Leu Glu Tyr Glu
            180                 185                 190
Ala Arg Gln Ile Arg Val Ala Met Glu Glu Gln Leu Gly Thr Cys Gln
            195                 200                 205
Asp Met Glu Lys Arg Ala Gln Arg Arg Ile Ala Arg Ile Gln Gln Ile
            210                 215                 220
Glu Lys Asp Ile Leu Arg Ile Arg Gln Leu Leu Gln Ser Gln Ala Thr
225                 230                 235                 240
Glu Ala Glu Arg Ser Ser Gln Asn Lys His Glu Thr Gly Ser His Asp
                245                 250                 255
Ala Glu Arg Gln Asn Glu Gly Gln Gly Val Gly Glu Ile Asn Met Ala
            260                 265                 270
Thr Ser Gly Asn Gly Gln Gly Ser Thr Thr Arg Met Asp His Glu Thr
            275                 280                 285
Ala Ser Val Leu Ser Ser Ser Thr His Ser Ala Pro Arg Arg Leu
            290                 295                 300
Thr Ser His Leu Gly Thr Lys Val Glu Met Val Tyr Ser Leu Leu Ser
305                 310                 315                 320
Met Leu Gly Thr His Asp Lys Asp Asp Met Ser Arg Thr Leu Leu Ala
                325                 330                 335
Met Ser Ser Ser Gln Asp Ser Cys Ile Ser Met Arg Gln Ser Gly Cys
            340                 345                 350
Leu Pro Leu Leu Ile Gln Leu Leu His Gly Asn Asp Lys Asp Ser Val
            355                 360                 365
Leu Leu Gly Asn Ser Arg Gly Ser Lys Glu Ala Arg Ala Arg Ala Ser
370                 375                 380
Ala Ala Leu His Asn Ile Ile His Ser Gln Pro Asp Asp Lys Arg Gly
385                 390                 395                 400
Arg Arg Glu Ile Arg Val Leu His Leu Leu Glu Gln Ile Arg Ala Tyr
                405                 410                 415
Cys Glu Thr Cys Trp Glu Trp Gln Glu Ala His Glu Pro Gly Met Asp
            420                 425                 430
Gln Asp Lys Asn Pro Met Pro Ala Pro Val Glu His Gln Ile Cys Pro
            435                 440                 445
Ala Val Cys Val Leu Met Lys Leu Ser Phe Asp Glu Glu His Arg His
            450                 455                 460
Ala Met Asn Glu Leu Gly Gly Leu Gln Ala Ile Ala Glu Leu Leu Gln
465                 470                 475                 480
Val Asp Cys Glu Met Tyr Gly Leu Thr Asn Asp His Tyr Ser Ile Thr
                485                 490                 495
Leu Arg Arg Tyr Ala Gly Met Ala Leu Thr Asn Leu Thr Phe Gly Asp
            500                 505                 510
```

-continued

```
Val Ala Asn Lys Ala Thr Leu Cys Ser Met Lys Gly Cys Met Arg Ala
            515                 520                 525
Leu Val Ala Gln Leu Lys Ser Glu Ser Glu Asp Leu Gln Gln Val Ile
        530                 535                 540
Ala Ser Val Leu Arg Asn Leu Ser Trp Arg Ala Asp Val Asn Ser Lys
545                 550                 555                 560
Lys Thr Leu Arg Glu Val Gly Ser Val Lys Ala Leu Met Glu Cys Ala
                565                 570                 575
Leu Glu Val Lys Lys Glu Ser Thr Leu Lys Ser Val Leu Ser Ala Leu
            580                 585                 590
Trp Asn Leu Ser Ala His Cys Thr Glu Asn Lys Ala Asp Ile Cys Ala
        595                 600                 605
Val Asp Gly Ala Leu Ala Phe Leu Val Gly Thr Leu Thr Tyr Arg Ser
610                 615                 620
Gln Thr Asn Thr Leu Ala Ile Glu Ser Gly Gly Gly Ile Leu Arg
625                 630                 635                 640
Asn Val Ser Ser Leu Ile Ala Thr Asn Glu Asp His Arg Gln Ile Leu
                645                 650                 655
Arg Glu Asn Asn Cys Leu Gln Thr Leu Leu Gln His Leu Lys Ser His
            660                 665                 670
Ser Leu Thr Ile Val Ser Asn Ala Cys Gly Thr Leu Trp Asn Leu Ser
        675                 680                 685
Ala Arg Asn Pro Lys Asp Gln Glu Ala Leu Trp Asp Met Gly Ala Val
690                 695                 700
Ser Met Leu Lys Asn Leu Ile His Ser Lys His Lys Met Ile Ala Met
705                 710                 715                 720
Gly Ser Ala Ala Ala Leu Arg Asn Leu Met Ala Asn Arg Pro Ala Lys
                725                 730                 735
Tyr Lys Asp Ala Asn Ile Met Ser Pro Gly Ser Ser Leu Pro Ser Leu
            740                 745                 750
His Val Arg Lys Gln Lys Ala Leu Glu Ala Glu Leu Asp Ala Gln His
        755                 760                 765
Leu Ser Glu Thr Phe Asp Asn Ile Asp Asn Leu Ser Pro Lys Ala Ser
770                 775                 780
His Arg Ser Lys Gln Arg His Lys Gln Ser Leu Tyr Gly Asp Tyr Val
785                 790                 795                 800
Phe Asp Thr Asn Arg His Asp Asp Asn Arg Ser Asp Asn Phe Asn Thr
                805                 810                 815
Gly Asn Met Thr Val Leu Ser Pro Tyr Leu Asn Thr Thr Val Leu Pro
            820                 825                 830
Ser Ser Ser Ser Ser Arg Gly Ser Leu Asp Ser Ser Arg Ser Glu Lys
        835                 840                 845
Asp Arg Ser Leu Glu Arg Glu Arg Gly Ile Gly Leu Gly Asn Tyr His
850                 855                 860
Pro Ala Thr Glu Asn Pro Gly Thr Ser Ser Lys Arg Gly Leu Gln Ile
865                 870                 875                 880
Ser Thr Thr Ala Ala Gln Ile Ala Lys Val Met Glu Glu Val Ser Ala
                885                 890                 895
Ile His Thr Ser Gln Glu Asp Arg Ser Ser Gly Ser Thr Thr Glu Leu
            900                 905                 910
His Cys Val Thr Asp Glu Arg Asn Ala Leu Arg Arg Ser Ser Ala Ala
        915                 920                 925
His Thr His Ser Asn Thr Tyr Asn Phe Thr Lys Ser Glu Asn Ser Asn
```

-continued

```
            930                 935                 940
Arg Thr Cys Ser Met Pro Tyr Ala Lys Leu Glu Tyr Lys Arg Ser Ser
945                 950                 955                 960

Asn Asp Ser Leu Asn Ser Val Ser Ser Ser Asp Gly Tyr Gly Lys Arg
                965                 970                 975

Gly Gln Met Lys Pro Ser Ile Glu Ser Tyr Ser Glu Asp Asp Glu Ser
                980                 985                 990

Lys Phe Cys Ser Tyr Gly Gln Tyr Pro Ala Asp Leu Ala His Lys Ile
                995                1000                1005

His Ser Ala Asn His Met Asp Asp Asn Asp Gly Glu Leu Asp Thr Pro
            1010                1015                1020

Ile Asn Tyr Ser Leu Lys Tyr Ser Asp Glu Gln Leu Asn Ser Gly Arg
1025                1030                1035                1040

Gln Ser Pro Ser Gln Asn Glu Arg Trp Ala Arg Pro Lys His Ile Ile
                1045                1050                1055

Glu Asp Glu Ile Lys Gln Ser Glu Gln Arg Gln Ser Arg Asn Gln Ser
                1060                1065                1070

Thr Thr Tyr Pro Val Tyr Thr Glu Ser Thr Asp Lys His Leu Lys
                1075                1080                1085

Phe Gln Pro His Phe Gly Gln Gln Glu Cys Val Ser Pro Tyr Arg Ser
                1090                1095                1100

Arg Gly Ala Asn Gly Ser Glu Thr Asn Arg Val Gly Ser Asn His Gly
1105                1110                1115                1120

Ile Asn Gln Asn Val Ser Gln Ser Leu Cys Gln Glu Asp Asp Tyr Glu
                1125                1130                1135

Asp Asp Lys Pro Thr Asn Tyr Ser Glu Arg Tyr Ser Glu Glu Glu Gln
                1140                1145                1150

His Glu Glu Glu Arg Pro Thr Asn Tyr Ser Ile Lys Tyr Asn Glu
                1155                1160                1165

Glu Lys Arg His Val Asp Gln Pro Ile Asp Tyr Ser Leu Lys Tyr Ala
                1170                1175                1180

Thr Asp Ile Pro Ser Gln Lys Gln Ser Phe Ser Phe Ser Lys Ser
1185                1190                1195                1200

Ser Ser Gly Gln Ser Ser Lys Thr Glu His Met Ser Ser Ser Ser Glu
                1205                1210                1215

Asn Thr Ser Thr Pro Ser Ser Asn Ala Lys Arg Gln Asn Gln Leu His
                1220                1225                1230

Pro Ser Ser Ala Gln Ser Arg Ser Gly Gln Pro Gln Lys Ala Ala Thr
                1235                1240                1245

Cys Lys Val Ser Ser Ile Asn Gln Glu Thr Ile Gln Thr Tyr Cys Val
                1250                1255                1260

Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
                1285                1290                1295

Asp Ser Ala Asn Thr Leu Gln Ile Ala Glu Ile Lys Glu Lys Ile Gly
                1300                1305                1310

Thr Arg Ser Ala Glu Asp Pro Val Ser Glu Val Pro Ala Val Ser Gln
                1315                1320                1325

His Pro Arg Thr Lys Ser Ser Arg Leu Gln Gly Ser Ser Leu Ser Ser
                1330                1335                1340

Glu Ser Ala Arg His Lys Ala Val Glu Phe Ser Ser Gly Ala Lys Ser
1345                1350                1355                1360
```

-continued

```
Pro Ser Lys Ser Gly Ala Gln Thr Pro Lys Ser Pro Glu His Tyr
        1365                1370                1375
Val Gln Glu Thr Pro Leu Met Phe Ser Arg Cys Thr Val Ser Ser
        1380                1385                1390
Leu Asp Ser Phe Glu Ser Arg Ser Ile Ala Ser Ser Val Gln Ser Glu
        1395                1400                1405
Pro Cys Ser Gly Met Val Ser Gly Ile Ile Ser Pro Ser Asp Leu Pro
        1410                1415                1420
Asp Ser Pro Gly Gln Thr Met Pro Pro Ser Arg Ser Lys Thr Pro Pro
1425                1430                1435                1440
Pro Pro Pro Gln Thr Ala Gln Thr Lys Arg Glu Val Pro Lys Asn Lys
            1445                1450                1455
Ala Pro Thr Ala Glu Lys Arg Glu Ser Gly Pro Lys Gln Ala Ala Val
        1460                1465                1470
Asn Ala Ala Val Gln Arg Val Gln Val Leu Pro Asp Ala Asp Thr Leu
        1475                1480                1485
Leu His Phe Ala Thr Glu Ser Thr Pro Asp Gly Phe Ser Cys Ser Ser
        1490                1495                1500
Ser Leu Ser Ala Leu Ser Leu Asp Glu Pro Phe Ile Gln Lys Asp Val
1505                1510                1515                1520
Glu Leu Arg Ile Met Pro Pro Val Gln Glu Asn Asp Asn Gly Asn Glu
        1525                1530                1535
Thr Glu Ser Glu Gln Pro Lys Glu Ser Asn Glu Asn Gln Glu Lys Glu
        1540                1545                1550
Ala Glu Lys Thr Ile Asp Ser Glu Lys Asp Leu Leu Asp Asp Ser Asp
        1555                1560                1565
Asp Asp Asp Ile Glu Ile Leu Glu Glu Cys Ile Ile Ser Ala Met Pro
1570                1575                1580
Thr Lys Ser Ser Arg Lys Ala Lys Lys Pro Ala Gln Thr Ala Ser Lys
1585                1590                1595                1600
Leu Pro Pro Pro Val Ala Arg Lys Pro Ser Gln Leu Pro Val Tyr Lys
        1605                1610                1615
Leu Leu Pro Ser Gln Asn Arg Leu Gln Pro Gln Lys His Val Ser Phe
        1620                1625                1630
Thr Pro Gly Asp Asp Met Pro Arg Val Tyr Cys Val Glu Gly Thr Pro
        1635                1640                1645
Ile Asn Phe Ser Thr Ala Thr Ser Leu Ser Asp Leu Thr Ile Glu Ser
        1650                1655                1660
Pro Pro Asn Glu Leu Ala Ala Gly Glu Gly Val Arg Gly Gly Ala Gln
1665                1670                1675                1680
Ser Gly Glu Phe Glu Lys Arg Asp Thr Ile Pro Thr Glu Gly Arg Ser
        1685                1690                1695
Thr Asp Glu Ala Gln Gly Gly Lys Thr Ser Ser Val Thr Ile Pro Glu
        1700                1705                1710
Leu Asp Asp Asn Lys Ala Glu Glu Gly Asp Ile Leu Ala Glu Cys Ile
        1715                1720                1725
Asn Ser Ala Met Pro Lys Gly Lys Ser His Lys Pro Phe Arg Val Lys
        1730                1735                1740
Lys Ile Met Asp Gln Val Gln Gln Ala Ser Ala Ser Ser Ser Ala Pro
1745                1750                1755                1760
Asn Lys Asn Gln Leu Asp Gly Lys Lys Lys Pro Thr Ser Pro Val
        1765                1770                1775
```

-continued

```
Lys Pro Ile Pro Gln Asn Thr Glu Tyr Arg Thr Arg Val Arg Lys Asn
            1780                1785                1790

Ala Asp Ser Lys Asn Asn Leu Asn Ala Glu Arg Val Phe Ser Asp Asn
        1795                1800                1805

Lys Asp Ser Lys Lys Gln Asn Leu Lys Asn Asn Ser Lys Asp Phe Asn
        1810                1815                1820

Asp Lys Leu Pro Asn Asn Glu Asp Arg Val Arg Gly Ser Phe Ala Phe
1825                1830                1835                1840

Asp Ser Pro His His Tyr Thr Pro Ile Glu Gly Thr Pro Tyr Cys Phe
            1845                1850                1855

Ser Arg Asn Asp Ser Leu Ser Ser Leu Asp Phe Asp Asp Asp Val
            1860                1865                1870

Asp Leu Ser Arg Glu Lys Ala Glu Leu Arg Lys Ala Lys Glu Asn Lys
        1875                1880                1885

Glu Ser Glu Ala Lys Val Thr Ser His Thr Glu Leu Thr Ser Asn Gln
        1890                1895                1900

Gln Ser Ala Asn Lys Thr Gln Ala Ile Ala Lys Gln Pro Ile Asn Arg
1905                1910                1915                1920

Gly Gln Pro Lys Pro Ile Leu Gln Lys Gln Ser Thr Phe Pro Gln Ser
            1925                1930                1935

Ser Lys Asp Ile Pro Asp Arg Gly Ala Ala Thr Asp Glu Lys Leu Gln
            1940                1945                1950

Asn Phe Ala Ile Glu Asn Thr Pro Val Cys Phe Ser His Asn Ser Ser
            1955                1960                1965

Leu Ser Ser Leu Ser Asp Ile Asp Gln Glu Asn Asn Asn Lys Glu Asn
        1970                1975                1980

Glu Pro Ile Lys Glu Thr Glu Pro Pro Asp Ser Gln Gly Glu Pro Ser
1985                1990                1995                2000

Lys Pro Gln Ala Ser Gly Tyr Ala Pro Lys Ser Phe His Val Glu Asp
            2005                2010                2015

Thr Pro Val Cys Phe Ser Arg Asn Ser Ser Leu Ser Ser Leu Ser Ile
            2020                2025                2030

Asp Ser Glu Asp Asp Leu Leu Gln Glu Cys Ile Ser Ser Ala Met Pro
        2035                2040                2045

Lys Lys Lys Lys Pro Ser Arg Leu Lys Gly Asp Asn Glu Lys His Ser
        2050                2055                2060

Pro Arg Asn Met Gly Gly Ile Leu Gly Glu Asp Leu Thr Leu Asp Leu
2065                2070                2075                2080

Lys Asp Ile Gln Arg Pro Asp Ser Glu His Gly Leu Ser Pro Asp Ser
            2085                2090                2095

Glu Asn Phe Asp Trp Lys Ala Ile Gln Glu Gly Ala Asn Ser Ile Val
            2100                2105                2110

Ser Ser Leu His Gln Ala Ala Ala Ala Cys Leu Ser Arg Gln Ala
        2115                2120                2125

Ser Ser Asp Ser Asp Ser Ile Leu Ser Leu Lys Ser Gly Ile Ser Leu
        2130                2135                2140

Gly Ser Pro Phe His Leu Thr Pro Asp Gln Glu Glu Lys Pro Phe Thr
2145                2150                2155                2160

Ser Asn Lys Gly Pro Arg Ile Leu Lys Pro Gly Glu Lys Ser Thr Leu
            2165                2170                2175

Glu Thr Lys Lys Ile Glu Ser Glu Ser Lys Gly Ile Lys Gly Gly Lys
            2180                2185                2190

Lys Val Tyr Lys Ser Leu Ile Thr Gly Lys Val Arg Ser Asn Ser Glu
```

-continued

```
           2195                2200               2205
Ile Ser Gly Gln Met Lys Gln Pro Leu Gln Ala Asn Met Pro Ser Ile
        2210                2215               2220

Ser Arg Gly Arg Thr Met Ile His Ile Pro Gly Val Arg Asn Ser Ser
2225                2230               2235               2240

Ser Ser Thr Ser Pro Val Ser Lys Lys Gly Pro Pro Leu Lys Thr Pro
                2245               2250               2255

Ala Ser Lys Ser Pro Ser Glu Gly Gln Thr Ala Thr Thr Ser Pro Arg
        2260               2265               2270

Gly Ala Lys Pro Ser Val Lys Ser Glu Leu Ser Pro Val Ala Arg Gln
        2275               2280               2285

Thr Ser Gln Ile Gly Gly Ser Ser Lys Ala Pro Ser Arg Ser Gly Ser
        2290               2295               2300

Arg Asp Ser Thr Pro Ser Arg Pro Ala Gln Gln Pro Leu Ser Arg Pro
2305                2310               2315               2320

Ile Gln Ser Pro Gly Arg Asn Ser Ile Ser Pro Gly Arg Asn Gly Ile
                2325               2330               2335

Ser Pro Pro Asn Lys Leu Ser Gln Leu Pro Arg Thr Ser Ser Pro Ser
                2340               2345               2350

Thr Ala Ser Thr Lys Ser Ser Gly Ser Gly Lys Met Ser Tyr Thr Ser
        2355               2360               2365

Pro Gly Arg Gln Met Ser Gln Gln Asn Leu Thr Lys Gln Thr Gly Leu
        2370               2375               2380

Ser Lys Asn Ala Ser Ser Ile Pro Arg Ser Glu Ser Ala Ser Lys Gly
2385                2390               2395               2400

Leu Asn Gln Met Asn Asn Gly Asn Gly Ala Asn Lys Lys Val Glu Leu
                2405               2410               2415

Ser Arg Met Ser Ser Thr Lys Ser Ser Gly Ser Glu Ser Asp Arg Ser
                2420               2425               2430

Glu Arg Pro Val Leu Val Arg Gln Ser Thr Phe Ile Lys Glu Ala Pro
        2435               2440               2445

Ser Pro Thr Leu Arg Arg Lys Leu Glu Glu Ser Ala Ser Phe Glu Ser
        2450               2455               2460

Leu Ser Pro Ser Ser Arg Pro Ala Ser Pro Thr Arg Ser Gln Ala Gln
2465                2470               2475               2480

Thr Pro Val Leu Ser Pro Ser Leu Pro Asp Met Ser Leu Ser Thr His
                2485               2490               2495

Ser Ser Val Gln Ala Gly Gly Trp Arg Lys Leu Pro Pro Asn Leu Ser
                2500               2505               2510

Pro Thr Ile Glu Tyr Asn Asp Gly Arg Pro Ala Lys Arg His Asp Ile
        2515               2520               2525

Ala Arg Ser His Ser Glu Ser Pro Ser Arg Leu Pro Ile Asn Arg Ser
        2530               2535               2540

Gly Thr Trp Lys Arg Glu His Ser Lys His Ser Ser Ser Leu Pro Arg
2545                2550               2555               2560

Val Ser Thr Trp Arg Arg Thr Gly Ser Ser Ser Ser Ile Leu Ser Ala
                2565               2570               2575

Ser Ser Glu Ser Ser Glu Lys Ala Lys Ser Glu Asp Glu Lys His Val
                2580               2585               2590

Asn Ser Ile Ser Gly Thr Lys Gln Ser Lys Glu Asn Gln Val Ser Ala
                2595               2600               2605

Lys Gly Thr Trp Arg Lys Ile Lys Glu Asn Glu Phe Ser Pro Thr Asn
        2610               2615               2620
```

```
Ser Thr Ser Gln Thr Val Ser Gly Ala Thr Asn Gly Ala Glu Ser
2625                2630                2635                2640

Lys Thr Leu Ile Tyr Gln Met Ala Pro Ala Val Ser Lys Thr Glu Asp
            2645                2650                2655

Val Trp Val Arg Ile Glu Asp Cys Pro Ile Asn Asn Pro Arg Ser Gly
        2660                2665                2670

Arg Ser Pro Thr Gly Asn Thr Pro Val Ile Asp Ser Val Ser Glu
    2675                2680                2685

Lys Ala Asn Pro Asn Ile Lys Asp Ser Lys Asp Asn Gln Ala Lys Gln
2690                2695                2700

Asn Val Gly Asn Gly Ser Val Pro Met Arg Thr Val Gly Leu Glu Asn
2705                2710                2715                2720

Arg Leu Asn Ser Phe Ile Gln Val Asp Ala Pro Asp Gln Lys Gly Thr
            2725                2730                2735

Glu Ile Lys Pro Gly Gln Asn Asn Pro Val Pro Val Ser Glu Thr Asn
            2740                2745                2750

Glu Ser Ser Ile Val Glu Arg Thr Pro Phe Ser Ser Ser Ser Ser
        2755                2760                2765

Lys His Ser Ser Pro Ser Gly Thr Val Ala Ala Arg Val Thr Pro Phe
    2770                2775                2780

Asn Tyr Asn Pro Ser Pro Arg Lys Ser Ser Ala Asp Ser Thr Ser Ala
2785                2790                2795                2800

Arg Pro Ser Gln Ile Pro Thr Pro Val Asn Asn Asn Thr Lys Lys Arg
            2805                2810                2815

Asp Ser Lys Thr Asp Ser Thr Glu Ser Ser Gly Thr Gln Ser Pro Lys
            2820                2825                2830

Arg His Ser Gly Ser Tyr Leu Val Thr Ser Val Lys Arg Gly Arg Met
        2835                2840                2845

Lys Leu Arg Lys Phe Tyr Val Asn Tyr Asn Cys Tyr Ile Asp Ile Leu
    2850                2855                2860

Phe Gln Met Lys Leu Lys Thr Glu Lys Phe Cys Lys Val Phe Leu Leu
2865                2870                2875                2880

Glu Gly Phe Cys Ser Gly Ser His Ile Tyr Thr Leu Ser Ser Leu Val
            2885                2890                2895

Leu Phe Trp Glu Ala Leu Leu Met Val Arg Lys Lys Ile Val Lys Pro
            2900                2905                2910

Ser Met Phe Val Gln Tyr Val Leu His Val Phe Lys Val Ala Pro Ile
        2915                2920                2925

Pro Thr Ser Phe Asn Tyr Cys Leu Ser Asn Asn Glu His Tyr Arg Lys
    2930                2935                2940

Ile Tyr Ile Ala Val Ile Asn His Phe Ile Ile Asn Leu Asn Leu His
2945                2950                2955                2960

Gln Gly Lys Ile Gly Ile Tyr Ala Lys Lys Asn Val Phe
        2965                2970

<210> SEQ ID NO 8
<211> LENGTH: 486
<212> TYPE: PRT
<213> ORGANISM: Homo sapiens

<400> SEQUENCE: 8

Met Pro Gln Leu Asp Ser Gly Gly Gly Ala Gly Gly Gly Asp Asp
 1               5                  10                  15

Leu Gly Ala Pro Asp Glu Leu Leu Ala Phe Gln Asp Glu Gly Glu Glu
```

-continued

```
                20                  25                  30
Gln Asp Asp Lys Ser Arg Asp Ser Ala Gly Pro Glu Arg Asp Leu Ala
                35                  40                  45
Glu Leu Lys Ser Ser Leu Val Asn Glu Ser Glu Gly Ala Ala Gly Ser
 50                  55                  60
Ala Gly Ile Pro Gly Val Pro Gly Ala Gly Ala Gly Ala Arg Gly Glu
 65                  70                  75                  80
Ala Glu Ala Leu Gly Arg Glu His Arg Ala Gln Arg Leu Phe Pro Asp
                85                  90                  95
Lys Leu Pro Glu Pro Leu Glu Asp Gly Leu Lys Ala Pro Glu Cys Thr
                100                 105                 110
Ser Gly Met Tyr Lys Glu Thr Val Tyr Ser Ala Phe Asn Leu Leu Met
                115                 120                 125
His Tyr Pro Pro Pro Ser Gly Ala Gly Gln His Pro Gln Pro Gln Pro
                130                 135                 140
Pro Leu His Lys Ala Asn Gln Pro Pro His Gly Val Pro Gln Leu Ser
145                 150                 155                 160
Leu Tyr Glu His Phe Asn Ser Pro His Pro Thr Pro Ala Pro Ala Asp
                165                 170                 175
Ile Ser Gln Lys Gln Val His Arg Pro Leu Gln Thr Pro Asp Leu Ser
                180                 185                 190
Gly Phe Tyr Ser Leu Thr Ser Gly Ser Met Gly Gln Leu Pro His Thr
                195                 200                 205
Val Ser Trp Pro Ser Pro Pro Leu Tyr Pro Leu Ser Pro Ser Cys Gly
                210                 215                 220
Tyr Arg Gln His Phe Pro Ala Pro Thr Ala Ala Pro Gly Ala Pro Tyr
225                 230                 235                 240
Pro Arg Phe Thr His Pro Ser Leu Met Leu Gly Ser Gly Val Pro Gly
                245                 250                 255
His Pro Ala Ala Ile Pro His Pro Ala Ile Val Pro Pro Ser Gly Lys
                260                 265                 270
Gln Glu Leu Gln Pro Phe Asp Arg Asn Leu Lys Thr Gln Ala Glu Ser
                275                 280                 285
Lys Ala Glu Lys Glu Ala Lys Lys Pro Thr Ile Lys Lys Pro Leu Asn
                290                 295                 300
Ala Phe Met Leu Tyr Met Lys Glu Met Arg Ala Lys Val Ile Ala Glu
305                 310                 315                 320
Cys Thr Leu Lys Glu Ser Ala Ala Ile Asn Gln Ile Leu Gly Arg Arg
                325                 330                 335
Trp His Ala Leu Ser Arg Glu Glu Gln Ala Lys Tyr Tyr Glu Leu Ala
                340                 345                 350
Arg Lys Glu Arg Gln Leu His Met Gln Leu Tyr Pro Gly Trp Ser Ala
                355                 360                 365
Arg Asp Asn Tyr Gly Lys Lys Arg Arg Ser Arg Glu Lys His Gln
                370                 375                 380
Glu Ser Thr Thr Gly Gly Lys Arg Asn Ala Phe Gly Thr Tyr Pro Glu
385                 390                 395                 400
Lys Ala Ala Ala Pro Ala Pro Phe Leu Pro Met Thr Val Leu Ala Ala
                405                 410                 415
Pro Gly Pro Gln Leu Pro Arg Thr His Pro His Thr Ile Cys Cys Pro
                420                 425                 430
Ala Ser Pro Gln Asn Cys Leu Leu Ala Leu Arg Ser Arg His Leu His
                435                 440                 445
```

-continued

Pro Gln Val Ser Pro Leu Leu Ser Ala Ser Gln Pro Gln Gly Pro His
     450                 455                 460

Arg Pro Pro Ala Ala Pro Cys Arg Ala His Arg Tyr Ser Asn Arg Asn
465                 470                 475                 480

Leu Arg Asp Arg Trp Pro
                485

<210> SEQ ID NO 9
<211> LENGTH: 511
<212> TYPE: PRT
<213> ORGANISM: Homo sapiens

<400> SEQUENCE: 9

Met Pro Gln Leu Asp Ser Gly Gly Gly Ala Gly Gly Gly Asp Asp
 1               5                  10                  15

Leu Gly Ala Pro Asp Glu Leu Leu Ala Phe Gln Asp Glu Gly Glu Glu
             20                  25                  30

Gln Asp Asp Lys Ser Arg Asp Ser Ala Gly Pro Glu Arg Asp Leu Ala
         35                  40                  45

Glu Leu Lys Ser Ser Leu Val Asn Glu Ser Glu Gly Ala Ala Gly Ser
 50                  55                  60

Ala Gly Ile Pro Gly Val Pro Gly Ala Gly Ala Arg Gly Glu
65                   70                  75                  80

Ala Glu Ala Leu Gly Arg Glu His Arg Ala Gln Arg Leu Phe Pro Asp
             85                  90                  95

Lys Leu Pro Glu Pro Leu Glu Asp Gly Leu Lys Ala Pro Glu Cys Thr
            100                 105                 110

Ser Gly Met Tyr Lys Glu Thr Val Tyr Ser Ala Phe Asn Leu Leu Met
        115                 120                 125

His Tyr Pro Pro Pro Ser Gly Ala Gly Gln His Pro Gln Pro Gln Pro
    130                 135                 140

Pro Leu His Lys Ala Asn Gln Pro Pro His Gly Val Pro Gln Leu Ser
145                 150                 155                 160

Leu Tyr Glu His Phe Asn Ser Pro His Pro Thr Pro Ala Pro Ala Asp
                165                 170                 175

Ile Ser Gln Lys Gln Val His Arg Pro Leu Gln Thr Pro Asp Leu Ser
            180                 185                 190

Gly Phe Tyr Ser Leu Thr Ser Gly Ser Met Gly Gln Leu Pro His Thr
        195                 200                 205

Val Ser Trp Pro Ser Pro Pro Leu Tyr Pro Leu Ser Pro Ser Cys Gly
    210                 215                 220

Tyr Arg Gln His Phe Pro Ala Pro Thr Ala Ala Pro Gly Ala Pro Tyr
225                 230                 235                 240

Pro Arg Phe Thr His Pro Ser Leu Met Leu Gly Ser Gly Val Pro Gly
                245                 250                 255

His Pro Ala Ala Ile Pro His Pro Ala Ile Val Pro Pro Ser Gly Lys
            260                 265                 270

Gln Glu Leu Gln Pro Phe Asp Arg Asn Leu Lys Thr Gln Ala Glu Ser
        275                 280                 285

Lys Ala Glu Lys Glu Ala Lys Lys Pro Thr Ile Lys Lys Pro Leu Asn
    290                 295                 300

Ala Phe Met Leu Tyr Met Lys Glu Met Arg Ala Lys Val Ile Ala Glu
305                 310                 315                 320

Cys Thr Leu Lys Glu Ser Ala Ala Ile Asn Gln Ile Leu Gly Arg Arg

```
                              325                 330                    335
Trp His Ala Leu Ser Arg Glu Gln Ala Lys Tyr Tyr Glu Leu Ala
                340                 345                 350
Arg Lys Glu Arg Gln Leu His Met Gln Leu Tyr Pro Gly Trp Ser Ala
                355                 360                 365
Arg Asp Asn Tyr Gly Lys Lys Lys Arg Arg Ser Arg Glu Lys His Gln
            370                 375                 380
Glu Ser Thr Thr Asp Pro Gly Ser Pro Lys Lys Cys Arg Ala Arg Phe
385                 390                 395                 400
Gly Leu Asn Gln Gln Thr Asp Trp Cys Gly Pro Cys Arg Arg Lys Lys
                405                 410                 415
Lys Cys Ile Arg Tyr Leu Pro Gly Glu Gly Arg Cys Pro Ser Pro Val
                420                 425                 430
Pro Ser Asp Asp Ser Ala Leu Gly Cys Pro Gly Ser Pro Ala Pro Gln
                435                 440                 445
Asp Ser Pro Ser Tyr His Leu Leu Pro Arg Phe Pro Thr Glu Leu Leu
                450                 455                 460
Thr Ser Pro Ala Glu Pro Ala Pro Thr Ser Pro Gly Leu Ser Thr Ala
465                 470                 475                 480
Leu Ser Leu Pro Thr Pro Gly Pro Pro Gln Ala Pro Arg Ser Thr Leu
                485                 490                 495
Gln Ser Thr Gln Val Gln Gln Gln Glu Ser Gln Arg Gln Val Ala
                500                 505                 510

<210> SEQ ID NO 10
<211> LENGTH: 20
<212> TYPE: PRT
<213> ORGANISM: Homo sapiens

<400> SEQUENCE: 10

Ser Tyr Leu Asp Ser Gly Ile His Ser Gly Ala Thr Thr Thr Ala Pro
1               5                   10                  15
Ser Leu Ser Gly
            20

<210> SEQ ID NO 11
<211> LENGTH: 21
<212> TYPE: PRT
<213> ORGANISM: Drosophila melanogaster

<400> SEQUENCE: 11

Ser Tyr Leu Gly Asp Ser Gly Ile His Ser Gly Ala Val Thr Gln Val
1               5                   10                  15
Pro Ser Leu Ser Gly
            20

<210> SEQ ID NO 12
<211> LENGTH: 15
<212> TYPE: DNA
<213> ORGANISM: Homo sapiens

<400> SEQUENCE: 12
ccctttgatc ttacc                                                          15

<210> SEQ ID NO 13
<211> LENGTH: 15
<212> TYPE: DNA
<213> ORGANISM: Homo sapiens
```

-continued

<400> SEQUENCE: 13
ccctttggcc ttacc                                                          15

<210> SEQ ID NO 14
<211> LENGTH: 8056
<212> TYPE: DNA
<213> ORGANISM: Homo sapiens
<220> FEATURE:
<221> NAME/KEY: TATA_signal
<222> LOCATION: (2458)...(2462)

<400> SEQUENCE: 14

```
agcttgtttg gccgttttag ggtttgttgg aattttttt tcgtctatgt acttgtgaat     60
tatttcacgt ttgccattac cggttctcca tagggtgatg ttcattagca gtggtgatag    120
gttaattttc accatctctt atgcggttga atagtcacct ctgaaccact ttttcctcca    180
gtaactcctc tttcttcgga ccttctgcag ccaacctgaa agaataacaa ggaggtggct    240
ggaaacttgt tttaaggaac cgcctgtcct tcccccgctg gaaaccttgc acctcggacg    300
ctcctgctcc tgcccccacc tgaccccgc cctcgttgac atccaggcgc gatgatctct    360
gctgccagta gagggcacac ttactttact ttcgcaaacc tgaacgcggg tgctgcccag    420
agaggggcg gagggaaaga cgctttgcag caaaatccag catagcgatt ggttgctccc    480
cgcgtttgcg gcaaaggcct ggaggcagga gtaatttgca atccttaaag ctgaattgtg    540
cagtgcatcg gatttggaag ctactatatt cacttaaac ttgaacgctg agctgcaaac    600
tcaacgggta ataacccatc ttgaacagcg tacatgctat acacgcaccc ctttccccg    660
aattgttttc tcttttggag gtggtggagg gagagaaaag tttacttaaa atgcctttgg    720
gtgagggacc aaggatgaga agaatgtttt ttgtttttca tgccgtggaa taacacaaaa    780
taaaaaatcc cgagggaata tacattatat attaaatata gatcatttca gggagcaaac    840
aaatcatgtg tggggctggg caactagcta agtcgaagcg taaataaaat gtgaatacac    900
gtttgcgggt tacatacagt gcactttcac tagtattcag aaaaaattgt gagtcagtga    960
actaggaaat taatgcctgg aaggcagcca aattttaatt aactcaagac tccccccccc   1020
ccaaaaaaag gcacggaagt aatactcctc tcctcttctt tgatcagaat cgatgcattt   1080
tttgtgcatg accgcatttc caataataaa aggggaaaga ggacctggaa aggaattaaa   1140
cgtccggttt gtccgggag gaaagagtta acggttttt tcacaagggt ctctgctgac   1200
tccccggct cggtccacaa gctctccact tgcccctttt aggaagtccg gtcccgcggt   1260
tcgggtaccc cctgccccctc ccatattctc ccgtctagca cctttgattt ctcccaaacc   1320
cggcagcccg agactgttgc aaaccggcgc cacagggcgc aaaggggatt tgtctcttct   1380
gaaacctggc tgagaaattg ggaactccgt gtgggaggcg tgggggtggg acggtgggt    1440
acagactggc agagagcagg caacctccct ctcgccctag tccagctctg gaacaggcag   1500
acacatctca gggctaaaca gacgcctccc gcacgggcc ccacggaagc ctgagcaggc    1560
ggggcaggag gggcggtatc tgctgctttg gcagcaaatt gggggactca gtctgggtgg   1620
aaggtatcca atccagatag ctgtgcatac ataatgcata atacatgact ccccccaaca   1680
aatgcaatgg gagtttattc ataacgcgct ctccaagtat acgtggcaat gcgttgctgg   1740
gttattttaa tcattctagg catcgttttc ctccttatgc ctctatcatt cctccctatc   1800
tacactaaca tcccacgctc tgaacgcgcg cccattaata ccttctttc ctccactctc   1860
cctgggactc ttgatcaaag cgcggcccctt tccccagcct tagcgaggcg ccctgcagcc   1920
```

-continued

```
tggtacgcgc gtggcgtggc ggtgggcgcg cagtgcgttc tcggtgtgga gggcagctgt    1980
tccgcctgcg atgatttata ctcacaggac aaggatgcgg tttgtcaaac aatactgcta    2040
cggaggagca gcagagaaag ggagagggtt tgagagggga caaaagaaaa tggtaggcgc    2100
gcgtagttaa ttcatgcggc tctcttactc tgtttacatc ctagagctag agtgctcggc    2160
tgcccggctg agtctcctcc ccaccttccc caccctcccc accctcccca taagcgcccc    2220
tcccgggttc ccaaagcaga gggcgtgggg gaaaagaaaa aagatcctct ctcgctaatc    2280
tccgcccacc ggcccttat aatgcgaggg tctggacggc tgaggacccc cgagctgtgc     2340
tgctcgcggc cgccaccgcc gggccccggc cgtccctggc tcccctcctg cctcgagaag    2400
ggcagggctt ctcagaggct tggcgggaaa agaacggag ggagggatcg cgctgagtat     2460
aaaagccggt tttcggggct ttatctaact cgctgtagta attccagtga gaggcagagg    2520
gagcgagcgg gcggccggct aggtggaag agccgggcga gcagagctgc gctgcgggcg     2580
tcctgggaag ggagatccgg agcgaatagg gggcttcgcc tctggcccag acctcccgct    2640
gatcccccag gcagcggtcc gcaacccttg ccgcatccac gaaactttgc ccatagcagc    2700
gggcggacac tttgcactgg aactgacaac acccgaccaa ggacgcgact ctcccgacgc    2760
ggggaggcta ttctgcccat ttggggacac ttccccgccg ctgccaggac ccgcttctct    2820
gaaaggctct ccttgcagct gcttagatac tgaatttttt tcgggaagtg gaaaaccagg    2880
taagcatcga agtccacttg tcttttaatt tacttttta tcagtttaat tctgagatga     2940
gtcgaatgcc taaatagggt gtcttttctc ccaatcctgc gttattgaca cctttctcgg    3000
ggtgggggtt attccagaat tggatcgggg tacagtgact tgtcaagatg ggggaggaga    3060
agacagaggg aaaacgggaa tggtttttac gattatcctt tcgagatttc tgccttatga    3120
atatattcac gtcgactccc ggccggtcgg acattcctac tttattgtgt taattgttct    3180
ctgggttttg ggggcgggg ggttgctttg cggtgggcag aaagtcccctt gcatcttgag    3240 ctccttggag aagggaccgc atatcgcctg tgtgagccag atcgctccgc aggcgctgac    3300
ttgtccccgt ctccgggagg gcagttaaat ctcgactcac cgcatttctg acagccggag    3360
acggacactg cggcgcgtcc cgcccgcctg tccccgcggc gattccaacc cgccctgatt    3420
cttttaagaa gttgacattt ggcttttaa aaagcaataa aacaatttaa aacctgggtc     3480
tctagaagtg ttaggacgtg gtgttgggta ggcgcaggca ggggaaaagg gaggcgagga    3540
tgtgtccgat tctcctgcaa tcgttgactt ggaaaaacca gggcgaatct ccgcacccag    3600
tcctgactcc cctgccgcgg ccgccctcgg gtgtcctcgc gcccgagatg cggaggaact    3660
gcgaggagcg gggctctggg cggttccaaa acagctgcta cccttggtgg ggtggctccg    3720
ggggaggtat cgcagcgggg tctctggcgc agttgcatct ccgtattgag tgcgaaggga    3780
ggtgccccta ttattatttg acacccccct tgtatttatg gagggtgtt aaagtccgcg     3840 gctgagctcg ccactccagc cggcgagaga agaagaaaa gctggcaaaa ggagtgttgg     3900 acggggcag tactggggt ggggacgggg gcggtggaga gggaaggttg ggagggctg       3960 cggtgccggc gggggtagga gagcgcctag gcgcgagtg ggaacagccg cagcggaggg     4020 gccccgcgc ggagcgggt tcacgcagcc gctttcgccc aggcgccttt cgccttctcc     4080
ttcaggtggc gcaaaacttt gtgccttgga ttttggcaaa ttgtattcct caccgccacc    4140
tcccgcggct tcttaagggc gccagggccg atttcgattc ctctgccgct gcggggccga    4200
ctcccgggct ttgcgctccg ggctcccggg ggagcggggg ctcggcgggt accaagacgc    4260
tggttcacta agtgcgtctc cgagatagca ggggactgtc caaaggggggt gaaagggtgc   4320
```

-continued

```
tcccttattt cccccaccaa gaccacccag ccgctttagg ggatagctct gcaaggggag   4380
aggttcggga ctgtggcgcg cactgcgcgc tgcgccaggt ttccgcacca agacccctttt  4440 aactcaagac tgcctcccgc tttgtgtgcc ccgctccagc agcctcccgc gacgatgccc   4500
ctcaacgtta gcttcaccaa caggaactat gacctcgact acgactcggt gcagccgtat   4560
ttctactgcg acgaggagga gaacttctac cagcagcagc agcagagcga actgcagccc   4620
ccggcgccca gcgaggatat ctggaagaaa ttcgagctgc tgcccacccc gcccctgtcc   4680
cctagccgcc gctccgggct ctgctcgccc tcctacgttg cggtcacacc cttctccctt   4740
cggggagaca cgacggcgg tggcgggagc ttctccacgg ccgaccagct ggagatggtg    4800
accgagctgc tgggaggaga catggtgaac cagagtttca tctgcgaccc ggacgacgag   4860
accttcatca aaacatcat catccaggac tgtatgtgga gcggcttctc ggccgccgcc    4920
aagctcgtct cagagaagct ggcctcctac caggctgcgc gcaaagacag cggcagcccg   4980
aaccccgccc gcggccacag cgtctgctcc acctccagct tgtacctgca ggatctgagc   5040
gccgccgcct cagagtgcat cgaccccctcg gtggtcttcc cctaccctct caacgacagc  5100
agctcgccca gtcctgcgc ctcgcaagac tccagcgcct tctctccgtc ctcggattct    5160
ctgctctcct cgacggagtc ctccccgcag ggcagcccccg agcccctggt gctccatgag  5220
gagacaccgc ccaccaccag cagcgactct ggtaagcgaa gcccgcccag gcctgtcaaa   5280
agtgggcggc tggatacctt tcccattttc attggcagct tatttaacgg gccactctta   5340
ttaggaagga gagatagcag atctggagag atttgggagc tcatcacctc tgaaaccttg   5400
ggctttagcg tttcctccca tcccttcccc ttagactgcc catgtttgca gccccctcc    5460 ccgtttgtct cccaccoctc aggaatttca tttaggtttt taaaccttct ggcttatctt   5520
acaactcaat ccacttcttc ttacctcccg ttaacatttt aattgccctg gggcggggtg   5580
gcagggagtg tatgaatgag gataagagag gattgatctc tgagagtgaa tgaattgctt   5640
ccctcttaac ttccgagaag tggtgggatt taatgaacta tctacaaaaa tgaggggctg   5700
tgtttagagg ctaggcaggg cctgcctgag tgcgggagcc agtgaactgc ctcaagagtg   5760
ggtgggctga ggagctggga tcttctcagc ctatttgaa cactgaaaag caaatccttg    5820
ccaaagttgg acttttttt tctttttattc cttccccccgc cctcttggac ttttggcaaa  5880 actgcaatt tttttttttt tattttttcat ttccagtaaa ataggagtt gctaaagtca   5940 taccaagcaa tttgcagcta tcatttgcaa cacctgaagt gttcttggta aagtccctca   6000
aaaataggag gtgcttggga atgtgctttg ctttgggtgt gtccaaagcc tcattaagtc   6060
ttaggtaaga attggcatca atgtcctatc ctgggaagtt gcacttttct tgtccatgcc   6120
ataacccagc tgtctttccc tttatgagac tcttaccttc atggtgagag gagtaagggt   6180
ggctggctag attggttctt ttttttttt tttccttttt taagacggag tctcactctg    6240
tcactaggct ggagtgcagt ggcgcaatca acctccaacc ccctggttca agagattctc   6300
ctgcctcagc ctcccaagta gctgggacta caggtgcaca ccaccatgcc aggctaattt   6360
ttgtaatttt agtagagatg gggtttcatc gtgttggcca ggatggtctc tcctgacctc   6420
acgatccgcc cacctcggcc tcccaaagtg ctgggattac aggtgtgagc cagggcacca   6480
ggcttagatg tggctctttg gggagataat tttgtccaga gacctttcta acgtattcat   6540
gccttgtatt tgtacagcat taatctggta attgattatt ttaatgtaac cttgctaaag   6600
gagtgatttc tatttccttt cttaaagagg aggaacaaga agatgaggaa gaaatcgatg   6660
```

```
ttgtttctgt ggaaaagagg caggctcctg gcaaaaggtc agagtctgga tcaccttctg      6720
ctggaggcca cagcaaacct cctcacagcc cactggtcct caagaggtgc cacgtctcca      6780
cacatcagca caactacgca gcgcctccct ccactcggaa ggactatcct gctgccaaga      6840
gggtcaagtt ggacagtgtc agagtcctga gacagatcag caacaaccga aaatgcacca      6900
gccccaggtc ctcggacacc gaggagaatg tcaagaggcg aacacacaac gtcttggagc      6960
gccagaggag gaacgagcta aaacggagct tttttgccct gcgtgaccag atcccggagt      7020
tggaaaacaa tgaaaaggcc cccaaggtag ttatccttaa aaaagccaca gcatacatcc      7080
tgtccgtcca agcagaggag caaaagctca tttctgaaga ggacttgttg cggaaacgac      7140
gagaacagtt gaaacacaaa cttgaacagc tacggaactc ttgtgcgtaa ggaaaagtaa      7200
ggaaaacgat tccttctaac agaaatgtcc tgagcaatcg cctatgaact tgtttcaaat      7260
gcatgatcaa atgcaacctc acaaccttgg ctgagtcttg agactgaaag atttagccat      7320
aatgtaaact gcctcaaatt ggactttggg cataaaagaa cttttttatg cttaccatct      7380 ttttttttc tttaacagat ttgtatttaa gaattgtttt taaaaaattt taagatttac      7440
acaatgtttc tctgtaaata ttgccattaa atgtaaataa ctttaataaa acgtttatag      7500
cagttacaca gaatttcaat cctagtatat agtacctagt attataggta ctataaaccc      7560 taatttttt tatttaagta cattttgctt tttaaagttg attttttct attgttttta       7620 gaaaaataa ataactggc aaatatatca ttgagccaaa tcttaagttg tgaatgtttt        7680
gtttcgtttc ttccccctcc caaccaccac catccctgtt tgttttcatc aattgcccct     7740
tcagagggtg gtcttaagaa aggcaagagt tttcctctgt tgaaatgggt ctggggggcct    7800 taaggtcttt aagttcttgg aggttctaag atgcttcctg gagactatga taacagccag     7860
agttgacagt tagaaggaat ggcagaaggc aggtgagaag gtgagaggta ggcaaaggag     7920
atacaagagg tcaaaggtag cagttaagta cacaaagagg cataaggact ggggagttgg    7980
gaggaaggtg aggaagaaac tcctgttact ttagttaacc agtgccagtc ccctgctcac    8040
tccaaaccca ggaatt                                                     8056

<210> SEQ ID NO 15
<211> LENGTH: 30
<212> TYPE: DNA
<213> ORGANISM: Homo sapiens

<400> SEQUENCE: 15
ctagctagcc tagcaccttt gatttctccc                                        30

<210> SEQ ID NO 16
<211> LENGTH: 30
<212> TYPE: DNA
<213> ORGANISM: Homo sapiens

<400> SEQUENCE: 16
cgtgatatcc gctttgatca agagtcccag                                        30

<210> SEQ ID NO 17
<211> LENGTH: 39
<212> TYPE: DNA
<213> ORGANISM: Homo sapiens

<400> SEQUENCE: 17
ctagctagca ctggtgcatc tcccaaaccc ggcagcccg                              39
```

```
<210> SEQ ID NO 18
<211> LENGTH: 40
<212> TYPE: DNA
<213> ORGANISM: Homo sapiens

<400> SEQUENCE: 18
ctggatatca ctggtgcatc ccagggagag tggaggaaag                              40

<210> SEQ ID NO 19
<211> LENGTH: 36
<212> TYPE: DNA
<213> ORGANISM: Homo sapiens

<400> SEQUENCE: 19
ctagcgcacc tttgatttct gcacctttga tttctg                                  36

<210> SEQ ID NO 20
<211> LENGTH: 36
<212> TYPE: DNA
<213> ORGANISM: Homo sapiens

<400> SEQUENCE: 20
ctagcagaaa tcaaggtgc agaaatcaaa ggtgcg                                   36

<210> SEQ ID NO 21
<211> LENGTH: 36
<212> TYPE: DNA
<213> ORGANISM: Homo sapiens

<400> SEQUENCE: 21
ctagcggact cttgatcaaa ggactcttga tcaaag                                  36

<210> SEQ ID NO 22
<211> LENGTH: 36
<212> TYPE: DNA
<213> ORGANISM: Homo sapiens

<400> SEQUENCE: 22
ctagctttga tcaagagtcc tttgatcaag agtccg                                  36

<210> SEQ ID NO 23
<211> LENGTH: 36
<212> TYPE: DNA
<213> ORGANISM: Homo sapiens

<400> SEQUENCE: 23
ctagcggact cttggccaaa ggactcttgg ccaaag                                  36

<210> SEQ ID NO 24
<211> LENGTH: 36
<212> TYPE: DNA
<213> ORGANISM: Homo sapiens

<400> SEQUENCE: 24
ctagctttgg ccaagagtcc tttggccaag agtccg                                  36

<210> SEQ ID NO 25
<211> LENGTH: 31
<212> TYPE: DNA
<213> ORGANISM: Homo sapiens

<400> SEQUENCE: 25
cgcggatccg cttccgtgtc caggttccct c                                       31
```

```
<210> SEQ ID NO 26
<211> LENGTH: 33
<212> TYPE: DNA
<213> ORGANISM: Homo sapiens

<400> SEQUENCE: 26
cgggaattcc tagcctagca ggttcgggga ggg                              33

<210> SEQ ID NO 27
<211> LENGTH: 36
<212> TYPE: DNA
<213> ORGANISM: Homo sapiens

<400> SEQUENCE: 27
ctagcgcacc tttggcttct gcacctttgg cttctg                           36

<210> SEQ ID NO 28
<211> LENGTH: 36
<212> TYPE: DNA
<213> ORGANISM: Homo sapiens

<400> SEQUENCE: 28
ctagcagaac gcaaaggtgc agaacgcaaa ggtgcg                           36
```

We claim:

1. A method of determining the presence or absence in a cell of wild-type Adenomatous polyposis coli (APC) or a wild-type downstream protein in the APC transcription regulatory pathway, comprising the steps of:
   introducing a Tcf-responsive reporter gene into the cell, wherein the Tcf-responsive reporter gene comprises a Tcf-binding element of c-MYC; and
   measuring transcription of said reporter gene; wherein a cell which supports active transcription of said reporter gene does not have wild-type APC or a downstream protein in the APC transcription regulatory pathway.

2. The method of claim 1 wherein the Tcf-responsive reporter gene comprises a Tcf binding element selected from the group consisting of TBE1 (CTTTGAT), TBE2 (ATCAAAG), and combinations thereof.

3. The method of claim 1 wherein the Tcf-responsive reporter gene comprises nucleotides -1194 to -484 of c-MYC (SEQ ID NO:14).

4. The method of claim 1 wherein the Tcf-responsive reporter gene comprises nucleotides -1194 to -741 of c-MYC (SEQ ID NO:14).

5. The method of claim 1 wherein the Tcf-responsive reporter gene comprises nucleotides -741 to -484 of c-MYC (SEQ ID NO:14).

6. A method of determining the presence or absence in a cell of wild-type APC, comprising the steps of:
   contacting a Tcf-responsive reporter gene with a lysate of the cell, wherein the Tcf-responsive reporter gene comprises a Tcf-binding element of c-MYC; and
   measuring transcription of said reporter gene; wherein a lysate which inhibits said transcription has wild-type APC.

7. The method of claim 6 wherein the Tcf-responsive reporter gene comprises a Tcf binding element selected from the group consisting of TBE1 (CTTTGAT), TBE2 (ATCAAAG), and combinations thereof.

8. The method of claim 6 wherein the Tcf-responsive reporter gene comprises nucleotides -1194 to -484 of c-MYC (SEQ ID NO:14).

9. The method of claim 6 wherein the Tcf-responsive reporter gene comprises nucleotides -1194 to -741 of c-MYC (SEQ ID NO:14).

10. The method of claim 6 wherein the Tcf-responsive reporter gene comprises nucleotides -741 to -484 of c-MYC (SEQ ID NO:14).

11. A method of identifying candidate drugs for use in Familial Adenomatous Polyposis (FAP) patients, patients with APC or β-catenin mutations, or patients with increased risk of developing colorectal cancer, comprising the steps of:
   contacting a cell having a Tcf-responsive reporter gene and having no wild-type APC or a mutant β-catenin with a test compound, wherein the Tcf-responsive reporter gene comprises a Tcf-binding element of c-MYC;
   measuring transcription of a Tcf-responsive reporter gene, wherein a test compound which inhibits the transcription of the reporter gene is a candidate drug for colorectal cancer therapy.

12. The method of claim 11 wherein the Tcf-responsive reporter gene comprises a Tcf binding element selected from the group consisting of TBE1 (CTTTGAT), TBE2 (ATCAAAG), and combinations thereof.

13. The method of claim 11 wherein the Tcf-responsive reporter gene comprises nucleotides -1194 to -484 of c-MYC (SEQ ID NO:14).

14. The method of claim 11 wherein the Tcf-responsive reporter gene comprises nucleotides -1194 to -741 of c-MYC (SEQ ID NO:14).

15. The method of claim 11 wherein the Tcf-responsive reporter gene comprises nucleotides -741 to -484 of c-MYC (SEQ ID NO:14).

16. The method of claim 11 wherein the cell produces an APC protein defective in β-catenin binding or regulation.

17. The method of claim 11 wherein the cell produces a β-catenin protein which is super-active, or which is defective in APC binding or resistant to APC regulation.

18. The method of claim 11 wherein the cell produces no detectable APC protein.

19. A method of identifying candidate drugs for use in FAP patients, patients with APC or β-catenin mutations, or patients with increased risk of developing colorectal cancer, comprising the steps of:

contacting a Tcf-responsive reporter gene which comprises a Tcf-binding element of c-MYC with a test compound under conditions in which the reporter gene is transcribed in the absence of the test compound; and measuring transcription of the Tcf-responsive reporter gene; wherein a test compound which inhibits said transcription is a candidate drug for colorectal cancer therapy.

20. The method of claim 19 wherein the Tcf-responsive reporter gene comprises a Tcf binding element selected from the group consisting of TBE1 (CTTTGAT), TBE2 (ATCAAAG), and combinations thereof.

21. The method of claim 19 wherein the Tcf-responsive reporter gene comprises nucleotides -1194 to -484 of c-MYC (SEQ ID NO:14).

22. The method of claim 19 wherein the Tcf-responsive reporter gene comprises nucleotides -1194 to -741 of c-MYC (SEQ ID NO:14).

23. The method of claim 19 wherein the Tcf-responsive reporter gene comprises nucleotides -741 to -484 of c-MYC (SEQ ID NO:14).

24. The method of claim 19 wherein the step of contacting is performed in the presence of a lysate of a cell which has no wild-type APC.

25. The method of claim 19 wherein the step of contacting is performed in the presence of a lysate of a cell which has a mutant β-catenin defective in APC binding or resistant to APC regulation or which is super-active.

26. The method of claim 24 wherein the cell produces an APC protein defective in β-catenin binding or regulation.

\* \* \* \* \*

UNITED STATES PATENT AND TRADEMARK OFFICE
CERTIFICATE OF CORRECTION

PATENT NO.: 6,140,052

DATED: October 31, 2000

INVENTOR: Tung-Chuan HE, *et al.*

It is certified that an error appears in the above-identified patent and that said Letters Patent is hereby corrected as shown below:

On the front cover, in [54] title:

"CMYC is Regulated by TCF-4" has been replaced with
--C-MYC is Regulated by TCF-4--.

Signed and Sealed this

Twenty-ninth Day of May, 2001

*Attest:*

NICHOLAS P. GODICI

*Attesting Officer*    *Acting Director of the United States Patent and Trademark Office*